US012742164B2

(12) United States Patent
Li et al.

(10) Patent No.: US 12,742,164 B2
(45) Date of Patent: Sep. 22, 2026

(54) SPECIFIC HOST FACTOR OF HEPATITIS B VIRUS INFECTION, AND USE THEREOF

(71) Applicant: National Institute of Biological Sciences, Beijing, Beijing (CN)

(72) Inventors: Cong Li, Beijing (CN); Yixue Wang, Beijing (CN); Wenhui Li, Beijing (CN)

(73) Assignee: NATIONAL INSTITUTE OF BIOLOGICAL SCIENCES, BEIJING, Beijing (CN)

( * ) Notice: Subject to any disclaimer, the term of this patent is extended or adjusted under 35 U.S.C. 154(b) by 810 days.

(21) Appl. No.: 17/813,157

(22) Filed: Jul. 18, 2022

(65) Prior Publication Data

US 2023/0038883 A1 Feb. 9, 2023

Related U.S. Application Data

(63) Continuation-in-part of application No. PCT/CN2021/072742, filed on Jan. 19, 2021.

(30) Foreign Application Priority Data

Jan. 19, 2020 (CN) ......................... 202010059253.1

(51) Int. Cl.

| | |
|---|---|
| ***C12N 15/09*** | (2006.01) |
| ***A61K 38/16*** | (2006.01) |
| ***A61P 31/20*** | (2006.01) |
| ***C07K 14/705*** | (2006.01) |
| ***C12N 15/113*** | (2010.01) |

(52) U.S. Cl.
CPC .............. *C12N 15/09* (2013.01); *A61K 38/16* (2013.01); *A61P 31/20* (2018.01); *C07K 14/705* (2013.01); *C12N 15/1131* (2013.01)

(58) Field of Classification Search
None
See application file for complete search history.

(56) References Cited

PUBLICATIONS

GenBank: BC172421.1. Synthetic construct *Homo sapiens* clone IMAGE:100069115, MGC:199126 scavenger receptor class F, member 2 (SCARF2) mRNA, encodes complete protein. Dated Mar. 16, 2009.*

Ishii et al. SREC-II, a New Member of the Scavenger Receptor Type F Family, Trans-interacts with SREC-I through Its Extracellular Domain. The Journal of Biological Chemistry. vol. 277, No. 42, Issue of Oct. 18, pp. 39696-39702, 2002.*

Nikolaou et al. Optimizing human hepatocyte models for metabolic phenotype and function: effects of treatment with dimethyl sulfoxide (DMSO). Physiol Rep, 4 (21), 2016, e12944.*

Nakagawa et al. Hepatic CREB3L3 Controls Whole-Body Energy Homeostasis and Improves Obesity and Diabetes. Endocrinology 155: 4706-4719, 2014.*

GenBank: ABZ92411.1. cAMP responsive element binding protein 3-like 3, partial [synthetic construct]. Dated Jul. 26, 2016.*

Chen et al., “Involvement of Soluble Scavenger Receptor A in Suppression of T Cell Activation in Patients with Chronic Hepatitis B”, BMC Immunology, vol. 16, May 16, 2015, pp. 1-11.

Migliavacca et al., “Scavenger Receptor Class F Member 2 Isoform 1 Precursor [*Homo sapiens*]”, NCBI Reference Sequence: NP 699165.3, Retrieved from https://www.ncbi.nlm.nih.gov, Aug. 22, 2019, 1 page.

Application No. PCT/CN2021/072742 , International Search Report and Written Opinion, Mailed on Apr. 26, 2021, 14 pages. English Translation on pp. 1-7.

Terpstra et al., “Hepatic and Extrahepatic Scavenger Receptors Function in Relation to Disease”, Arteriosclerosis, Thrombosis, and Vascular Biology, vol. 20, Aug. 2000, pp. 1860-1872.

Application No. CN202180010050.6 , Office Action, Mailed on Jun. 9, 2023, 15 pages.

* cited by examiner

*Primary Examiner* — Nianxiang Zou
(74) *Attorney, Agent, or Firm* — Kilpatrick Townsend & Stockton LLP

(57) ABSTRACT

Provided is a host factor specific for hepatitis B virus (HBV) infection. The specific host factor CREBH can remarkably enhance HBV infection. The specific host factor can, on the one hand, enhance entry of HBV, and on the other hand, enhance transcription of HBV to some extent. In the CREBH regulatory pathway there is a specific host factor SCARF2. During HBV infection, an N-terminus EGF-like domain of SCARF2 plays a crucial role in the infection and entry of HBV. The two correlated specific host factors provide a new target for inhibiting HBV infection.

6 Claims, 16 Drawing Sheets

Specification includes a Sequence Listing.

SEQUENCE LISTING

```
Sequence total quantity: 15
SEQ ID NO: 1            moltype = AA  length = 461
FEATURE                 Location/Qualifiers
source                  1..461
                        mol_type = protein
                        organism = Homo sapiens
SEQUENCE: 1
MNTDLAAGKM ASAACSMDPI DSFELLDLLF DRQDGILRHV ELGEGWGHVK DQQVLPNPDS  60
DDFLSSILGS GDSLPSSPLW SPEGSDSGIS EDLPSDPQDT PPRSGPATSP AGCHPAQPGK  120
GPCLSYHPGN SCSTTTPGPV IQVPEASVTI DLEMWSPGGR ICAEKPADPV DLSPRCNLTV  180
KDLLLSGSSG DLQQHHLGAS YLLRPGAGHC QELVLTEDEK KLLAKEGITL PTQLPLTKYE  240
ERVLKKIRRK IRNKQSAQES RKKKKEYIDG LETRMSACTA QNQELQRKVL HLEKQNLSLL  300
EQLKKLQAIV VQSTSKSAQT GTCVAVLLLS FALIILPSIS PFGPNKTESP GDFAPVRVFS  360
RTLHNDAASR VAADAVPGSE APGPRPEADT TREESPGSPG ADWGFQDTAN LTNSTEELDN  420
ATLVLRNATE GLGQVALLDW VAPGPSTGSG RAGLEAAGDE L                     461

SEQ ID NO: 2            moltype = AA  length = 340
FEATURE                 Location/Qualifiers
source                  1..340
                        mol_type = protein
                        organism = synthetic construct
SEQUENCE: 2
MCLSYHPGNS CSTTTPGPVI QVPEASVTID LEMWSPGGRI CAEKPADPVD LSPRCNLTVK  60
DLLLSGSSGD LQQHHLGASY LLRPGAGHCQ ELVLTEDEKK LLAKEGITLP TQLPLTKYEE  120
RVLKKIRRKI RNKQSAQESR KKKKEYIDGL ETRMSACTAQ NQELQRKVLH LEKQNLSLLE  180
QLKKLQAIVV QSTSKSAQTG TCVAVLLLSF ALIILPSISP FGPNKTESPG DFAPVRVFSR  240
TLHNDAASRV AADAVPGSEA PGPRPEADTT REESPGSPGA DWGFQDTANL TNSTEELDNA  300
TLVLRNATEG LGQVALLDWV APGPSTGSGR AGLEAAGDEL                       340

SEQ ID NO: 3            moltype = AA  length = 197
FEATURE                 Location/Qualifiers
source                  1..197
                        mol_type = protein
                        organism = synthetic construct
SEQUENCE: 3
MCLSYHPGNS CSTTTPGPVI QVPEASVTID LEMWSPGGRI CAEKPADPVD LSPRCNLTVK  60
DLLLSGSSGD LQQHHLGASY LLRPGAGHCQ ELVLTEDEKK LLAKEGITLP TQLPLTKYEE  120
RVLKKIRRKI RNKQSAQESR KKKKEYIDGL ETRMSACTAQ NQELQRKVLH LEKQNLSLLE  180
QLKKLQAIVV QSTSKSA                                                197

SEQ ID NO: 4            moltype = AA  length = 108
FEATURE                 Location/Qualifiers
source                  1..108
                        mol_type = protein
                        organism = synthetic construct
SEQUENCE: 4
QELVLTEDEK KLLAKEGITL PTQLPLTKYE ERVLKKIRRK IRNKQSAQES RKKKKEYIDG  60
LETRMSACTA QNQELQRKVL HLEKQNLSLL EQLKKLQAIV VQSTSKSA              108

SEQ ID NO: 5            moltype = RNA  length = 19
FEATURE                 Location/Qualifiers
source                  1..19
                        mol_type = other RNA
                        organism = synthetic construct
SEQUENCE: 5
gctgctggaa agatggctt                                             19

SEQ ID NO: 6            moltype = RNA  length = 19
FEATURE                 Location/Qualifiers
source                  1..19
                        mol_type = other RNA
                        organism = synthetic construct
SEQUENCE: 6
gctcctggat ctcctgttt                                             19

SEQ ID NO: 7            moltype = RNA  length = 19
FEATURE                 Location/Qualifiers
source                  1..19
                        mol_type = other RNA
                        organism = synthetic construct
SEQUENCE: 7
ccctcttgga gcaactgaa                                             19
```

```
SEQ ID NO: 8            moltype = AA  length = 871
FEATURE                 Location/Qualifiers
source                  1..871
                        mol_type = protein
                        organism = Homo sapiens
SEQUENCE: 8
MEGAGPRGAG PARRRGAGGP PSPLLPSLLL LLLLWMLPDT VAPQELNPRG RNVCRAPGSQ  60
VPTCCAGWRQ QGDECGIAVC EGNSTCSENE VCVRPGECRC RHGYFGANCD TKCPRQFWGP  120
DCKELCSCHP HGQCEDVTGQ CTCHARRWGA RCEHACQCQH GTCHPRSGAC RCEPGWWGAQ  180
CASACYCSAT SRCDPQTGAC LCHAGWWGRS CNNQCACNSS PCEQQSGRCQ CRERTFGARC  240
DRYCQCFRGR CHPVDGTCAC EPGYRGKYCR EPCPAGFYGL GCRRRCGQCK GQQPCTVAEG  300
RCLTCEPGWN GTKCDQPCAT GFYGEGCSHR CPPCRDGHAC NHVTGKCTRC NAGWIGDRCE  360
TKCSNGTYGE DCAFVCADCG SGHCDFQSGR CLCSPGVHGP HCNVTCPPGL HGADCAQACS  420
CHEDTCDPVT GACHLETNQR KGVMGAGALL VLLVCLLLSL LGCCCACRGK DPTRRPRPRR  480
ELSLGRKKAP HRLCGRFSRI SMKLPRIPLR RQKLPKVVVA HHDLDNTLNC SFLEPPSGLE  540
QPSPSWSSRA SFSSFDTTDE GPVYCVPHEE APAESRDPEV PTVPAEAPAP SPVPLTTPAS  600
AEEAIPLPAS SDSERSASSV EGPGGALYAR VARREARPAR ARGEIGGLSL SPSPERRKPP  660
PPDPATKPKV SWIHGKHSAA AAGRAPSPPP PGSEAAPSPS KRKRTPSDKS AHTVEHGSPR  720
TRDPTPRPPG LPEEATALAA PSPPRARARG RGPGLLEPTD AGGPPRSAPE AASMLAAELR  780
GKTRSLGRAE VALGAQGPRE KPAPPQKAKR SVPPASPARA PPATETPGPE KAATDLPAPE  840
TPRKKTPIQK PPRKKSREAA GELGRAGAPT L                                871

SEQ ID NO: 9            moltype = AA  length = 333
FEATURE                 Location/Qualifiers
source                  1..333
                        mol_type = protein
                        organism = synthetic construct
SEQUENCE: 9
QGDECGIAVC EGNSTCSENE VCVRPGECRC RHGYFGANCD TKCPRQFWGP DCKELCSCHP  60
HGQCEDVTGQ CTCHARRWGA RCEHACQCQH GTCHPRSGAC RCEPGWWGAQ CASACYCSAT  120
SRCDPQTGAC LCHAGWWGRS CNNQCACNSS PCEQQSGRCQ CRERTFGARC DRYCQCFRGR  180
CHPVDGTCAC EPGYRGKYCR EPCPAGFYGL GCRRRCGQCK GQQPCTVAEG RCLTCEPGWN  240
GTKCDQPCAT GFYGEGCSHR CPPCRDGHAC NHVTGKCTRC NAGWIGDRCE TKCSNGTYGE  300
DCAFVCADCG SGHCDFQSGR CLCSPGVHGP HCN                              333

SEQ ID NO: 10           moltype = AA  length = 88
FEATURE                 Location/Qualifiers
source                  1..88
                        mol_type = protein
                        organism = synthetic construct
SEQUENCE: 10
SACYCSATSR CDPQTGACLC HAGWWGRSCN NQCACNSSPC EQQSGRCQCR ERTFGARCDR  60
YCQCFRGRCH PVDGTCACEP GYRGKYCR                                    88

SEQ ID NO: 11           moltype = RNA  length = 19
FEATURE                 Location/Qualifiers
source                  1..19
                        mol_type = other RNA
                        organism = synthetic construct
SEQUENCE: 11
gcgagaccaa gtgtagcaa                                              19

SEQ ID NO: 12           moltype = RNA  length = 19
FEATURE                 Location/Qualifiers
source                  1..19
                        mol_type = other RNA
                        organism = synthetic construct
SEQUENCE: 12
gtgacaggcc agtgtactt                                              19

SEQ ID NO: 13           moltype = RNA  length = 19
FEATURE                 Location/Qualifiers
source                  1..19
                        mol_type = other RNA
                        organism = synthetic construct
SEQUENCE: 13
cctgccacct agaaaccaa                                              19

SEQ ID NO: 14           moltype = RNA  length = 19
FEATURE                 Location/Qualifiers
source                  1..19
                        mol_type = other RNA
                        organism = synthetic construct
SEQUENCE: 14
tccttctcct cgtttgaca                                              19

SEQ ID NO: 15           moltype = RNA  length = 19
FEATURE                 Location/Qualifiers
```

-continued

| | |
|---|---|
| source | 1..19 |
| | mol_type = other RNA |
| | organism = synthetic construct |
| SEQUENCE: 15 | |
| gactgcaagg agctgtgta | 19 |

SPECIFIC HOST FACTOR OF HEPATITIS B VIRUS INFECTION, AND USE THEREOF

This application is a Continuation-in-part application of PCT/CN2021/072742, filed on Jan. 19, 2021, which claims priority to and the benefit of Chinese Patent Application No. 2020100592531, filed on Jan. 19, 2020. Said PCT application and Chinese application are incorporated herein by reference in their entireties for all purposes.

REFERENCE TO A SEQUENCE LISTING

The Sequence Listing written in file 109307-1340026-000100US_CIP Sequence Listing.xml created on Jul. 17, 2022, 16 KB, machine format IBM-PC, MS-Windows operating system, is hereby incorporated by reference in its entirety for all purposes.

FIELD OF THE INVENTION

The present invention relates to the field of disease mechanism research and drug research and development, and in particular to a host factor specific for HBV infection and use thereof.

BACKGROUND

Hepatitis B virus (HBV) is one of the most widely distributed viruses in the world. According to data from the World Health Organization in 2018, there were still 257 million people worldwide that were infected with HBV, and in 2015 alone, there were 880,000 people died from diseases caused by HBV. However so far, there have not been any targeted drugs that can be used to cure HBV infection. Commonly used drugs for treatment of hepatitis B include alpha-interferon (IFN-α) and nucleic acid (nucleotide) analogs represented by Entecavir. The genome of HBV is an open circular double-stranded DNA of approximately 3.2 kb, which includes a complete minus strand and an incomplete plus strand and is called a relaxed closed circular DNA (rcDNA). After HBV infects cells, the plus strand is complemented first, by way of which the rcDNA is repaired to form a covalently closed circular DNA (cccDNA). cccDNA can exist stably in host cell nucleus and serve as the transcriptional template for all viral gene products. Due to a special characteristic of cccDNA, i.e., being difficult to eradicate, cccDNA has become a core issue in research on curing of HBV infection. The genome of HBV itself is extremely simple, and the entire life process of virus replication is completed under coordinated action of host factors.

Gripon et al. found in 1993 that the addition of polyethylene glycol (PEG) to the in vitro primary human hepatocytes (PHHs) infection system could markedly increase HBV infection efficiency, while the addition of PEG after binding of the virus to cells could not enhance the infection; it was therefore speculated that PEG enhanced the binding of the virus to receptors on the cell membrane surface rather than the fusion of the virus with the cell membrane. In addition, it is known that the viral titer required for in vitro infection is much higher than the minimum virus dose required for initiating the infection in a gorilla infection model or under physiological conditions. A specific host factor is thus required for HBV in order to enhance the infection with the virus.

SUMMARY

The first objective of the present invention is to provide a host factor specific for HBV infection. The specific host factor has an amino acid sequence as shown in SEQ ID NO:1, or has an amino acid sequence having at least 90% identity to the amino acid sequence as shown in SEQ ID NO:1 and having activity as a host factor for HBV infection.

Existing HBV in vitro infection, of such as HepG2-NTCP cell line or primary human hepatocytes (PHHs), requires addition of 4%-5% PEG while adding the virus so as to enhance infection. The addition of PEG does not lead to fusion of the virus with cells, but enhancement of mutual contact between the virus and HSPG or NTCP. Nonetheless, even so, addition of the virus at a high titer is still required to achieve high-efficiency infection. In contrast to in vitro infection, in vivo infection does not require these conditions. With this significant difference in infection conditions, it is not difficult to speculate that in the in vitro infection system, after the virus binds to NTCP, there is still a lack of host factors that can facilitate entry of the virus. In order to discover and identify unknown host factors limiting the entry of the virus, the present invention selects, from liver-specifically expressed genes defined by the HPA database, 74 membrane proteins to construct a cDNA expression library. The present invention chooses to perform the infection in the presence of 1% PEG, screens the cDNA library, and then obtains CREBH gene through screening. Protein expressed by CREBH gene has an amino acid sequence as shown in SEQ ID NO:1.

CREBH (cAMP-responsive element-binding protein, hepatocyte specific) gene was first cloned and identified in 2001. It is classified into the CREB/ATF gene family due to its region exhibiting significant homology to the bZIP domain of members of the CREB/ATF gene family. Compared with other genes in the same family that are ubiquitously expressed, CREBH is liver-specifically expressed (hence the name). Later experiments found that CREBH was also expressed in small intestinal tissues. CREBH is similar in structure to gene ATF6 in the same family. CREBH and ATF6 both encode a transmembrane region within the genes, and are type II transmembrane proteins. A full-length gene is localized to the endoplasmic reticulum or Golgi membrane after being expressed, while a protein that lacks the transmembrane region is localized to the nucleus. Kezhong Zhang et al. in 2006 proved that CREBH can be transferred from the endoplasmic reticulum to the Golgi through the RIP (Regulated intramembrane proteolysis), and then cleaved by S1P (Site 1 protease) and S2P (Site 2 protease), releasing N-terminus domain of the protein into the nucleus, and thereby activating gene expression. Similar genes are for example SREBPs (sterol regulatory-element binding protein) which are key regulators in cholesterol and lipid metabolism.

As a preferred solution of the present invention, the specific host factor is a host factor specific for HBV entry into cells, or a host factor specific for HBV transcription, or a host factor specific for HBV entry into cells and HBV transcription. Specifically, in the present invention, in an experiment for detecting effects of CREBH after HBV infection, the necessity of a transcriptional activation domain is first determined by cloning a truncated form of CREBH. Second, results of Northern-blot analysis of HBV in CREBH-overexpressed cell lines also verify that CREBH can change the transcriptional state of HBV. This effect is more apparent in the presence of 5% PEG, which is likely because more cccDNAs are formed during the infection under this condition, i.e., transcription templates that CREBH can affect is more. However, compared with the transduction of CREBH after the infection as shown in the experiment, the transduction of CREBH before the infection exerts a more apparent enhancement effect on the infection in the presence of 1% PEG, indicating that CREBH enhances virus entry. These results illustrate the bifunctionality of CREBH, i.e., enhancing virus entry and HBV transcription. In addition, from results of HBcAg levels in HBV infection, the transduction of CREBH can increase the number of stained cells, and CREBH can remarkably enhance the infection with HBV at a low viral titer. All these support the enhancement effect of CREBH on virus entry.

The present invention seeks to further protect an activator of the specific host factor. As a preferred solution of the present invention, the activating factor is insulin. CREBH gene belongs to transmembrane proteins, and has transcriptional activation ability. CREBH has a gene structure that is roughly the same as that of ATF6 with which CREBH is highly homologous and needs to be cleaved to release the N-terminus domain to thereby fulfill its functions. However, compared with ATF6, CREBH has a much shorter C-terminus, and functions of its domains are yet unknown. Previous studies reported that the C-terminal domain of ATF6 gene is necessary for response to upstream ER stress signaling, and thus suggested that CREBH and ATF6 may be induced to be activated in response to different signal sources. However, in an experiment for screening of CREBH and subsequent verification experiments, in addition to the use of PMM medium, no treatment capable of activating CREBH was particularly added. Results of staining of CREBH and truncated forms thereof demonstrate separation of staining signals at the N-terminus and the C-terminus, indicating that CREBH has been activated by cleavage in the experiment of transducing CREBH for HBV infection. It has been reported that CREBH can be partially spontaneously activated by strong promoters such as CMV promoter, but most experiments on CREBH were performed in the presence of exogenous strong promoters, and no obvious spontaneous activation was observed. Therefore, in the present invention, the activation of CREBH after it being transduced is more likely to come from the stimulation of the PMM medium. The present invention verifies that DMSO and insulin in PMM may be the signal source for CREBH activation.

The present invention seeks to further protect a truncated form of the specific host factor, preferably an N-terminus domain of the specific host factor. As a preferred solution of the present invention, the N-terminus domain is residues 1-122 of CREBH protein (having an amino acid sequence as shown in SEQ ID NO:2), or residues 122-318 (having an amino acid sequence as shown in SEQ ID NO:3), or residues 1-122 and 122-318. As a preferred solution of the present invention, the N-terminus domain is residues 211-318 of CREBH protein (having an amino acid sequence as shown in SEQ ID NO:4). Specifically, in order to analyze the enhancement effect of each domain of CREBH on HBV infection, the present invention subjects CREBH to truncating mutation. Experiments on infection in the presence of truncated mutants clearly show that the transcriptional activation and DNA binding domains of CREBH are necessary. Unexpectedly, although clone CREBH-122 is partially removed of the transcriptional activation function structurally and functionally, it has the strongest enhancement effect on HBV infection. Analysis of mRNA sequencing results show that there are 109 genes that are up-regulated by more than 2 folds after transduction of CREBH, and 104 genes that are up-regulated by more than 2 folds after transduction of CREBH-122, but only 17 genes that are changed in the same way. This may be a result of the regionalized distribution of the N-terminal transcriptional activation domain of CREBH, but it cannot be ruled out the possibility that the activation of downstream genes caused by CREBH-122 is non-native activation. Regarding the effects of truncated clones of CREBH on the infection, in addition to the two clones CREBH-122 and CREBH-122-318 significantly enhancing the infection, it is also observed in the present invention that the shorter truncated form CREBH-211-318 exerts a slightly inhibiting effect on HVB infection. Because the bZIP domain in CREBH needs to dimerize into a homo- or heterodimer to bind DNA, and CREBH-211-318 clone expresses only the bZIP domain, it is speculated that this truncated form of CREBH, together with wild-type CREBH, will form a nonfunctional dimer to exert a dominant-negative effect. This result is consistent with the result of inhibition of the infection after CREBH knockdown.

The expression and cell membrane localization of NTCP are key factors in HBV infection. Therefore, in the present invention, for a factor affecting the infection, it must be determined first whether NTCP is changed. CREBH transduction down-regulates the transcriptional level of NTCP, but because the expression of NTCP in HepG2-NTCP cells is driven by the CMV promoter, it is not clear how CREBH affects the CMV promoter. CREBH does not alter the membrane localization of HepG2-NTCP-GFP. Myr47 polypeptide can also inhibit HBV infection in the CREBH transduced group or the PWPI empty control group, indicating that CREBH may be a relatively independent infection-limiting factor located downstream of NTCP.

Based on the above research and findings, the present invention seeks to further protect a nucleotide encoding the specific host factor or the truncated form of the specific host factor, as well as a vector into which the nucleotide has been inserted and/or which is capable of exogenously expressing the specific host factor or the truncated form of the specific host factor.

The present invention seeks to further protect HBV infection-susceptible cells into which the isolated nucleotide or the vector has been exogenously transferred. Preferably, the cells are selected from the group consisting of HepG2 cells, HepG2-NTCP cells, and PHHs. To realize activation of CREBH, the cells are preferably cultured in a medium containing DMSO and/or insulin, the medium being preferably PMM medium.

The present invention seeks to further protect use of the nucleotide or the vector in constructing non-human transgenic and CREBH gene knockout or CREBH gene exogenously expressed animal models, and in constructing non-human transgenic animal models infected with HBV or susceptible to HBV infection.

The present invention seeks to further protect use of the specific host factor, the truncated form, the activator, the nucleotide, the vector, the cells, or a non-human transgenic animal model constructed using the nucleotide or the vector, in screening of a drug for treatment and/or prevention of HBV infection and/or related diseases.

The present invention seeks to further protect a method for screening a drug for treatment and/or prevention of HBV infection or related diseases. The method includes: using the specific host factor, the truncated form, the activator, the nucleotide, the vector, the cells, or a non-human transgenic animal model constructed using the nucleotide or the vector.

The present invention seeks to further protect use of the specific host factor, the truncated form, the activator, the nucleotide, a substance capable of inhibiting or decreasing protein expression/function of the specific host factor or the truncated form, a substance capable of inhibiting or decreasing interaction between the specific host factor or the truncated form and HBV, and/or a substance capable of inhibiting or decreasing transcription of the nucleotide, in treatment and/or prevention of HBV infection and related diseases in mammals.

The present invention seeks to further protect a drug for treatment and/or prevention of HBV infection and related diseases in mammals. The drug comprises: the specific host factor, the truncated form, the activator, the nucleotide, a substance capable of inhibiting or decreasing protein expression/function of the specific host factor or the truncated form, a substance capable of inhibiting or decreasing interaction between the specific host factor or the truncated form and HBV, and/or a substance capable of inhibiting or decreasing transcription of the nucleotide.

As a preferred embodiment of the present invention, the drug comprises residues 211-318 of CREBH protein.

As a preferred embodiment of the present invention, the substance capable of reducing the transcription of the nucleotide may be dsRNA, siRNA, RNA interference vectors or RNA interference lentiviruses against the above isolated nucleotide.

As a preferred embodiment of the present invention, siRNA of the isolated nucleotide is selected from the group consisting of:

```
siCREBH-1 as shown in SEQ ID NO: 5:
gcugcuggaaagauggcuu;

siCREBH-2 as shown in SEQ ID NO: 6:
andgcuccuggaucuccuguuu;

siCREBH-3 as shown in SEQ ID NO: 7:
cccucuuggagcaacugaa.
```

As a preferred embodiment of the present invention, the drug comprises: an insulin inhibitor.

The second objective of the present invention is to protect another host factor specific for HBV infection. The specific host factor has an amino acid sequence as shown in SEQ ID NO:8, or has an amino acid sequence having at least 90% identity to the amino acid sequence as shown in SEQ ID NO:8 and having activity as a host factor for HBV infection.

A large number of experimental results provided in the present invention play a pivotal role in cloning and identification of gene SCARF2 downstream of CREBH. In the present invention, it is further found through experiments that SCARF2 is a major gene in enhancement of HBV infection by CREBH. Protein expressed by SCARF2 gene has an amino acid sequence as shown in SEQ ID NO:8.

SCARF2 belongs to the Scavenger receptor family. Members of the Scavenger receptor family are greatly different in their structures and are involved in different cytological functions. The concept of this family was first found and proposed by Goldstein et al. in 1979 when enabling macrophages to phagocytize acetylated low-density lipoproteins. Later, a series of modified low-density lipoprotein receptors were cloned and identified, and systematically categorized into subfamilies A, B, etc. according to sequence information. So far, all known genes of the Scavenger receptor family have been categorized into 8 subfamilies (A-H). There are three genes belonging to the F subfamily, namely SCARF1, SCARF2, and SCARF3. SCARF1 is a type I transmembrane protein, with multiple EGF-like domains at its N-terminus, and a long segment of unknown structure and function, in addition to a proline-rich segment, at the C-terminus. SCARF2 was identified in 2002. SCARF2 has a very similar genetic structure to SCARF1 and can interact with SCARF1, but its specific cytological function is unknown. The third gene, Megf10 (SCARF3), is considered a receptor for C1Q and is responsible for clearance of apoptotic cells.

As a preferred solution of the present invention, the specific host factor is a host factor specific for HBV entry into cells. Specifically, the present invention, by way of experiments such as co-floating with the virus, verifies that SCARF2 may directly interact with HBV particles and thus serves as one of co-receptors for entry of the virus into cells. As a preferred embodiment of the present invention, the specific host factor is a co-receptor for HBV entry into cells.

The present invention seeks to further protect a truncated form of the specific host factor. Preferably, the truncated form is an N-terminus domain of the specific host factor. As a preferred solution of the present invention, the N-terminus domain is an N-terminus epidermal growth factor-like (EGF-like) domain of SCARF2 protein, preferably having an amino acid sequence as shown in SEQ ID NO:9 or SEQ ID NO:10. Specifically, it is found through experiments in the present invention that N-terminus EGF-like domains of SCARF2 are necessary for enhancement of the infection. Although the EGF-like domains have relatively consistent three-dimensional structures each formed by three conserved pairs of disulfide bonds, they have very different functions in different proteins. Generally, EGF-like domains are believed to be involved in interaction between proteins. This function may also exist in enhancement of HBV infection by SCARF2.

Based on the above research and findings, the present invention seeks to further protect a nucleotide encoding the specific host factor or the truncated form of the specific host factor, as well as a vector into which the nucleotide has been inserted and/or which is capable of exogenously expressing the specific host factor or the truncated form of the specific host factor.

The present invention seeks to further protect HBV infection-susceptible cells into which the isolated nucleotide or the vector has been exogenously transferred. Preferably, the cells are selected from the group consisting of HepG2 cells, HepG2-NTCP cells, and primary human hepatocytes (PHHs).

The present invention seeks to further protect use of the nucleotide or the vector in constructing non-human transgenic and SCARF2 gene knockout or SCARF2 gene knock-in animal models, and in constructing non-human transgenic animal models infected with HBV or susceptible to HBV infection.

The present invention seeks to further protect use of the specific host factor, the truncated form, the nucleotide, the vector, the cells, or a non-human transgenic animal model constructed using the nucleotide or the vector, in screening of a drug for treatment and/or prevention of HBV infection and/or related diseases.

The present invention seeks to further protect a method for screening a drug for treatment and/or prevention of HBV infection or related diseases. The method includes: using the specific host factor, the truncated form, the nucleotide, the vector, the cells, or a non-human transgenic animal model constructed using the nucleotide or the vector.

The present invention seeks to further protect use of the specific host factor, the truncated form, the nucleotide, a substance capable of inhibiting or decreasing protein expression/function of the specific host factor or the truncated form, a substance capable of inhibiting or decreasing interaction between the specific host factor or the truncated form and HBV, a substance capable of inhibiting or decreasing transcription of the nucleotide, in treatment and/or prevention of HBV infection and related diseases in mammals.

The present invention seeks to further protect a drug for treatment and/or prevention of HBV infection and related diseases in mammals. The drug comprises: the specific host factor, the truncated form, the nucleotide, a substance capable of inhibiting or decreasing protein expression/function of the specific host factor or the truncated form, a substance capable of inhibiting or decreasing interaction between the specific host factor or the truncated form and HBV, and/or a substance capable of inhibiting or decreasing transcription of the nucleotide.

As a preferred embodiment of the present invention, the substance capable of decreasing transcription of the nucleotide may be dsRNA, siRNA, RNA interference vectors or RNA interference lentivirus against the isolated nucleotide.

As a preferred embodiment of the present invention, siRNA of the isolated nucleotide is selected from the group consisting of:

```
siSCARF2-1 as shown in SEQ ID NO: 11:
gcgagaccaaguguagcaa;

siSCARF2-2 as shown in SEQ ID NO: 12:
gugacaggccaguguacuu;

siSCARF2-3 as shown in SEQ ID NO: 13:
ccugccaccuagaaaccaa;

siSCARF2-4 as shown in SEQ ID NO: 14:
uccuucucccucguuugaca;
and

siSCARF2-5 as shown in SEQ ID NO: 15:
gacugcaaggagcugugua.
```

The third objective of the present invention is to protect a composite host factor for HBV infection. The composite host factor comprises the two specific host factors described above and/or their respective truncated forms.

The present invention seeks to further protect a vector system, into which a nucleotide sequence encoding the composite host factor or truncated form thereof has been inserted, and/or which is capable of exogenously expressing the composite host factor or truncated form thereof. Specifically, the vector system may comprise a vector A and a vector B. The vector A encodes and is capable of exogenously expressing the amino acid sequence as shown in SEQ ID NO:1, or an amino acid sequence having at least 90% identity to the amino acid sequence as shown in SEQ ID NO:1 and having activity as a host factor for HBV infection. The vector B encodes and is capable of exogenously expressing the amino acid sequence as shown in SEQ ID NO:8, or an amino acid sequence having at least 90% identity to the amino acid sequence as shown in SEQ ID NO:8 and having activity as a host factor for HBV infection.

The present invention seeks to further protect HBV infection-susceptible cells into which the vector system has been exogenously transferred. Preferably, the cells are selected from the group consisting of: HepG2 cells, HepG2-NTCP cells, and primary human hepatocytes (PHHs).

The present invention seeks to further protect use of a nucleotide sequence encoding the composite host factor or truncated form thereof or the vector system in constructing non-human transgenic animal models infected with HBV or susceptible to HBV infection.

The present invention seeks to further protect use of the composite host factor or truncated form thereof, a nucleotide sequence encoding the composite host factor or truncated form thereof, the vector system, the cells, or a non-human transgenic animal model constructed using the nucleotide sequence encoding the composite host factor or truncated form thereof or the vector system, in screening of a drug for treatment and/or prevention of HBV infection and/or related diseases.

The present invention seeks to further protect a method for screening a drug for treatment and/or prevention of HBV infection or related diseases. The method includes: using the composite host factor or truncated form thereof, the nucleotide sequence encoding the composite host factor or truncated form thereof, the vector system, the cells, or a non-human transgenic animal model constructed using the nucleotide sequence encoding the composite host factor or truncated form thereof or the vector system.

The present invention seeks to further protect use of the composite host factor or truncated form thereof, a nucleotide sequence encoding the composite host factor or truncated form thereof, a substance capable of inhibiting or decreasing protein expression/function of the composite host factor or truncated form thereof, a substance capable of inhibiting or decreasing interaction between the composite host factor or truncated form thereof and HBV, and/or a substance capable of inhibiting or decreasing transcription of the nucleotide sequence encoding the composite host factor or truncated form thereof, in treatment and/or prevention of HBV infection and related diseases in mammals.

The present invention seeks to further protect a drug for treatment and/or prevention of HBV infection and related diseases in mammals. The drug comprises: the composite host factor or truncated form thereof, a nucleotide sequence encoding the composite host factor or truncated form thereof, a substance capable of inhibiting or decreasing protein expression/function of the composite host factor or truncated form thereof, a substance capable of inhibiting or decreasing interaction between the composite host factor or truncated form thereof and HBV, and/or a substance capable of inhibiting or decreasing transcription of the nucleotide sequence encoding the composite host factor or truncated form thereof.

Specifically, the drug is a composition, and may comprise a drug against CREBH (e.g., dsRNA, siRNA, RNA interference vectors or RNA interference lentivirus against the nucleotide of the isolated CREBH, or residues 211-318 of CREBH protein) and a drug against SCARF2 (e.g., dsRNA, siRNA, RNA interference vectors or RNA interference lentivirus against the nucleotide of the isolated SCARF2).

As a preferred embodiment of the present invention, the substance capable of inhibiting or decreasing transcription of the nucleotide sequence encoding the composite host factor or truncated form thereof is selected from the group consisting of sequences as shown in SEQ ID NO:5, SEQ ID NO:6, SEQ ID NO:7, SEQ ID NO:11, SEQ ID NO:12, SEQ ID NO:13, SEQ ID NO:14, and SEQ ID NO:15.

In addition, the present invention verifies that the above-described host factors are all specific host factors for HBV, and that neither of CREBH and SCARF2 can enhance hepatitis D virus (HDV) infection. This phenomenon can be explained and discussed from the following aspects. First, the present invention finds that HDV infection is more dependent on the expression of NTCP on the cell membrane than HBV infection, and HDV infection can occur more easily at a low PEG concentration. Although HDV and HBV have the same viral outer membrane, HDV can be assembled in the absence of L protein. This indicates that the two are significantly different in later stages of the infection. Second, SCARF2 contains, at its C-terminus, a signal that can lead to its localization to the nuclear membrane, and a mutant with deletion of the C-terminal Proline-rich domain cannot enhance the infection. This suggests that the change in subcellular localization of SCARF2 might also have been involved in the process of the infection. Besides, results of ultracentrifugation show that SCARF2 bound to virus particles rather than subviral particles (SVP), and therefore it is speculated that SCARF2 might have mediated the virus entry process of HBV which is different from HDV.

Compared with the existing technologies, it is found in the present invention for the first time that SCARF2 can interact with the amino acids 69-108 of the preS1 segment on the surface of HBV, thereby functioning as an intracellular receptor during HBV entry. The above results provide one with understanding of the molecular mechanism of HBV entry from the present invention, and provide a new target for inhibiting HBV infection. More importantly, the present invention provides an important basis for the prevention and treatment of as well as drug screening for HBV infection and related diseases.

BRIEF DESCRIPTION OF THE DRAWINGS

(FIG. 3A) HbeAg level in infection in the presence of 1% PEG. (FIG. 3B) HbsAg level in infection in the presence of 1% PEG. (FIG. 3C) HbeAg level in infection in the presence of 5% PEG. (FIG. 3D) HBsAg level in infection in the presence of 5% PEG.

(FIG. 4A) Results of infection in the presence of 1% PEG. (FIG. 4B) Results of infection in the presence of 5% PEG. (FIG. 4C) A schematic diagram of relative infection percentages. Four groups namely 1% PEG CREBH-122 group, 1% PEG PWPI group, 5% PEG PWPI group, 5% PEG CREBH-122 group were selected for experiments. For each group, HBeAg level on Day 6 post infection at 100% virus infection was calculated as 100%, and infection values at other viral titers each were divided by this 100% to obtain the percentages of the relative infection percentages.

(FIG. 5A) HbeAg level in infection in the presence of 1% PEG. (FIG. 5B) HbsAg level in infection in the presence of 1% PEG. (FIG. 5C) HbeAg level in infection in the presence of 5% PEG. (FIG. 5D) HBsAg level in infection in the presence of 5% PEG.

(FIG. 6A) Three CREBH siRNAs were transfected into HepG2-NTCP cells. At 48 hours after the transfection, RNA was collected using TRIzol, and relative expression of CREBH was measured by reverse transcription. (FIG. 6B) HBeAg level in supernatant after HBV infection. (FIG. 6C) HBsAg level in supernatant after HBV infection.

(FIGS. 7A-7E) Changes in relative expression of SCARF2 mRNA after transduction of CREBH, CREBH-122, CREBH-122-318, CREBH-211-318, and CREBH-307, respectively. (FIG. 7F) Statistics for relative expression of SCARF2 mRNA in each group.

(FIG. 8A) HepG2-NTCP cells were transduced with SCARF2, CREBH-122, or PWPI, and then infected with HBV in the presence of 1% PEG. (FIG. 8B) HepG2-NTCP cells were transduced with SCARF2, CREBH-122, or PWPI, and then infected with HBV in the presence of 5% PEG. (FIG. 8C) Nuclear and cytoplasmic fractions of the cells at 0 hour, 6 hours, 24 hours, and 72 hours after infection were isolated, and content of HBV DNA in each of the fractions was detected by southern-blot.

(FIG. 9A) Five siRNAs of SCARF2 were designed and synthesized, and transfected into HepG2-NTCP cells. At 48 hours after the transfection, RNA was collected by TRIzol, and relative expression of SCARF2 was measured by reverse transcription. (FIG. 9B) Infection was conducted after SCARF2 was knocked down by siRNA. NTCP siRNA was used as a positive control. HbeAg in supernatant of the medium was detected. (FIG. 9C) Infection was conducted after SCARF2 was knocked down by siRNA. NTCP siRNA was used as a positive control. HBsAg in supernatant of the medium was detected.

(FIG. 10A) Schematic diagram showing structure of SCARF2 gene. (FIG. 10B) Results of N-terminal HA-tag staining after transducing AC12 cells with mutants with deletion of different EGF-like domains. (FIG. 10C) ELISA results of HBeAg levels in HBV infection occurred after transduction of different truncated forms. EGF4-6 was involved in change of localization of SCARF2 in cells and affected HBV infection.

(FIG. 11C) Infected cells were harvested for southern-blot detection of cccDNA. (FIG. 11D) Results of quantification of cccDNA in cells by cccDNA quantification.

(FIG. 12A) After addition of EGF4-6 protein, the peak position of virus fractions shifted backwards by 2 fractions. (FIG. 12B) Equilibrium density gradient centrifugation was performed after incubating EGF4-6 with the virus. The dotted line represents HBsAg level, and the solid line represents DNA copy numbers of the virus. The lower chart shows results of quantification of the protein in each of the fractions by ImageJ software after detection of content of EGF-6 protein in corresponding fractions.

(FIG. 13A) Results of specific binding of SCARF2 EGF4-6 protein to a polypeptide containing amino acids 69-108 of preS1 (peptide$^{69-108}$). (FIG. 13B) Results of measurement of dissociation constant ($K_d$) between the polypeptide and SCARF2 EGF4-6 protein.

(FIG. 14A) Interaction between NTCP and SCARF2 during HBV infection labeled by proximity ligation assay (PLA) (image on the left). PLA results obtained after HBV infection was blocked by using A14 antibody against HBV preS1 region (image on the right). HBV infection significantly increased the interaction between NTCP and SCARF2. (FIG. 14B) Subcellular localization of HBV DNA and SCARF2 protein in HepG2-NTCP cells at 48 hours (upper images) and 72 hours (lower images) after the cells were infected with HBV. HBV DNA in situ hybridization and SCARF2 protein immunofluorescence staining were performed. In the experiments of HBV infection, results of intracellular co-localization of the viral DNA and SCARF2 indicate that SCARF2 was involved in the process of HBV infection. Cell nuclei were stained with DAPI (A, B).

(FIG. 15A) After the stable expression of SCARF2-GFP in HepG2-NTCP cells, the position of SCARF2-GFP in subcellular localization changed 48 hours after HBV infection or HBV infection was blocked by A14. (FIG. 15B) SCARF2-GFP was overexpressed in HepG2-NTCP cells. Intracellular localization of SCARF2 in the cells was indicated by GFP signal, and meanwhile a nuclear pore complex on the nuclear membrane was indicated by immunofluorescently stained Nup153. "Transection" represents that the microscope is focused on a section of the nucleus. "Top" represents that the microscope is focused on the top of the nucleus. (FIG. 15C) Photographs obtained after reconstruction of SCARF2-GFP and Nup153 signals on the nuclear membrane using a Nikon SIM super-resolution microscope. (FIG. 15D) Schematic diagram showing localization of SCARF2-GFP, the nuclear pore complex, and HBV DNA signals after simultaneous observation thereof using a super-resolution microscope.

DETAILED DESCRIPTION OF THE EMBODIMENTS

The following embodiments are intended to illustrate the present invention, rather than limiting the scope of the present invention.

Example 1: Construction and Screening of a cDNA Library for Hepatocyte Membrane Protein Genes 1. Effects of PEG on Infection HepG2-NTCP (AC12) is an existing cell line that can be efficiently infected with HBV. It is a single clone selected and obtained in accordance with stable expression of NTCP in HepG2 cancer cell line. However, according to existing studies and data known in the laboratory, efficient HBV infection of HepG2-NTCP cells still requires additional addition of PEG (PEG8000) as well as a viral titer much higher than that required for in vivo infection. It is generally believed that the role of PEG is to enhance the contact between the virus and receptors on the cell membrane surface; meanwhile, the high viral titer used suggests that in cells cultured in vitro there may be host factors limiting the infection or a lack of infection-dependent host factors. Therefore, use of the virus at a low titer and use of PEG at a reduced concentration in genetic screening for the infection may help to obtain not only factors that can increase interaction between the virus and receptors on the cell membrane surface, but also key host factors for entry of the virus.

Experiments were conducted to first detect the infection of HepG2-NTCP cells in the presence of different concentrations of PEG. Results show that the infection of the HepG2-NTCP cells relies on the concentration of PEG added during the infection. The presence of 1% PEG and 2% PEG can lead to enhanced HBV infection, which however is much lower than the level of the infection achieved in the presence of 5% PEG.

2. Construction and Screening of a Library for Hepatocyte Membrane Proteins

The present invention consulted and utilized the Human Protein Atlas database for the definition and grouping of liver-specifically expressed genes. There were altogether 426 liver-specifically expressed genes. Because it was speculated that host-restrictive factors affecting the infection would be more likely to be located on the cell membrane or the endomembrane system, the present invention selected 114 membrane protein genes for cloning from the 426 genes by taking advantage of the annotated subcellular localization information. The membrane protein genes were cloned into a PWPI vector by enzyme digestion and ligation and then subjected to sequencing and verification, by way of which a target library containing 76 genes was successfully constructed.

Figure 1:
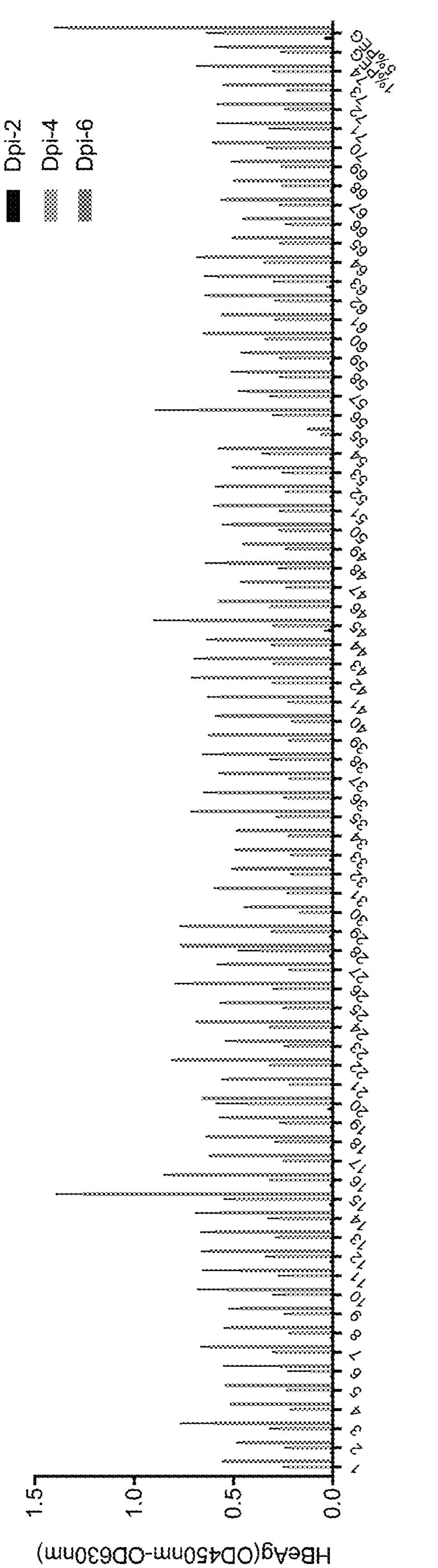
FIG. 1 shows the results of screening of a cDNA library in Example 1.

The cDNA library was prepared by packaging lentivirus, with HepG2-NTCP cells expressing the cDNA clones being packaged therein. After 24 hours, infection was conducted with HBV at a same tier in the presence of 1% PEG. Culture supernatant was collected every 2 days, and was tested with HBeAg and HBsAg kits. As can be seen from results shown in FIG. 1, clone No. 15 (CREBH) remarkably enhances HBV infection, and the HbeAg level is similar to that achieved in the infection in the presence of 5% PEG. Results of HBcA staining show that CREBH remarkably increases the number of HBcAg-positive cells, indicating that CREBH may enhance the infection efficiency.

Example 2: CREBH Versus HBV Infection

1. Expression Pattern of CREBH in Tissues

Clone No. 15 encoded CREBH (Cyclic AMP Response Element-binding Protein H, CREB3L3) gene. Referring to GTEx database for information of CREBH gene, CREBH is specifically expressed in liver and small intestine tissues, but its expression level in liver is much higher than that in small intestine tissues.

The expression levels of CREBH in HepG2-NTCP cells, mPHH (humanized mouse derived primary hepatocyte) cells, liver cancer tissues and adjacent normal tissues of patients were simultaneously measured in the experiments. The expression levels of CREBH in HepG2-NTCP cells and mPHH cells are close to each other but not high. The expression levels of CREBH in liver cancer tissues and adjacent normal tissues are significantly higher than those in the cell lines, and the expression level in liver cancer tissues is slightly higher than that in the adjacent normal tissues. This indicates that the expression of CREBH is inhibited in the cell lines cultured in vitro, which may be one of the reasons why in vitro infection efficiency is lower than in vivo infection efficiency.

2. Analysis of Functions of Truncated Forms of CREBH

Human CREBH consists of 461 amino acids and belongs to type II transmembrane protein. CREBH protein has, at its N-terminus, a bZIP domain that can bind to DNA and have a transmembrane region that can attach the protein to the endoplasmic reticulum membrane. Upon stimulated by a signal, CREBH can be transported to the Golgi membrane, where it is cleaved by Sire 1 Protease and Sire 2 Protease to release the N-terminus with a transcriptional activation function into the nucleus. Functions of the residual C-terminus are unknown. When it is comes to its regulatory functions, CREBH is often reported to be associated with lipid metabolism and cholesterol metabolism. Since the subcellular localization of domains at the two termini of CREBH are different, it is necessary to further detect which of the domains has the effect of enhancing HBV infection.

3. Results of CREBH Secondary Structure Prediction

Figure 2:
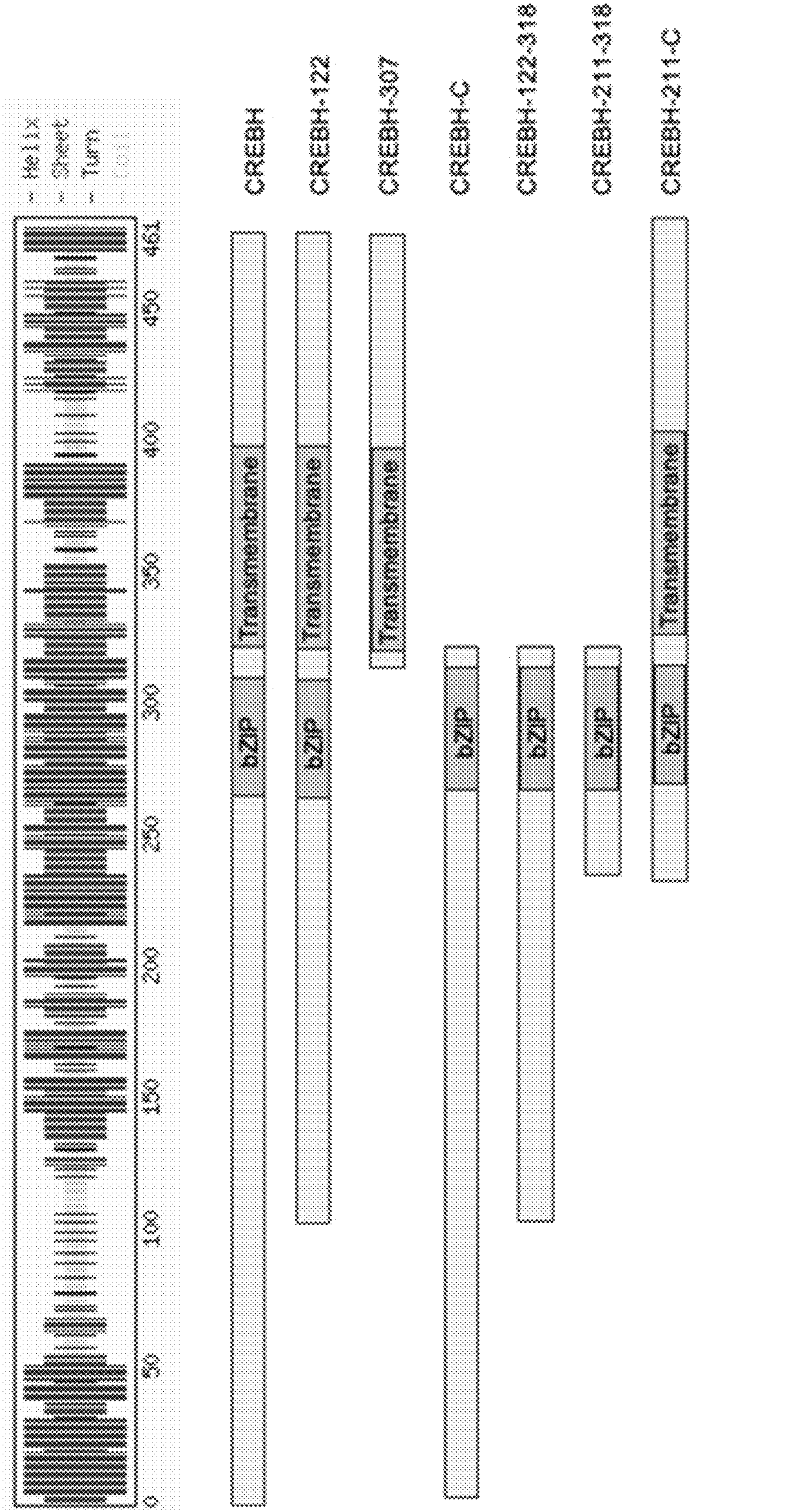
FIG. 2 is a schematic diagram showing the construction of truncated clones of CREBH in Example 2.
Figures 3A, 3B, 3C, 3D:
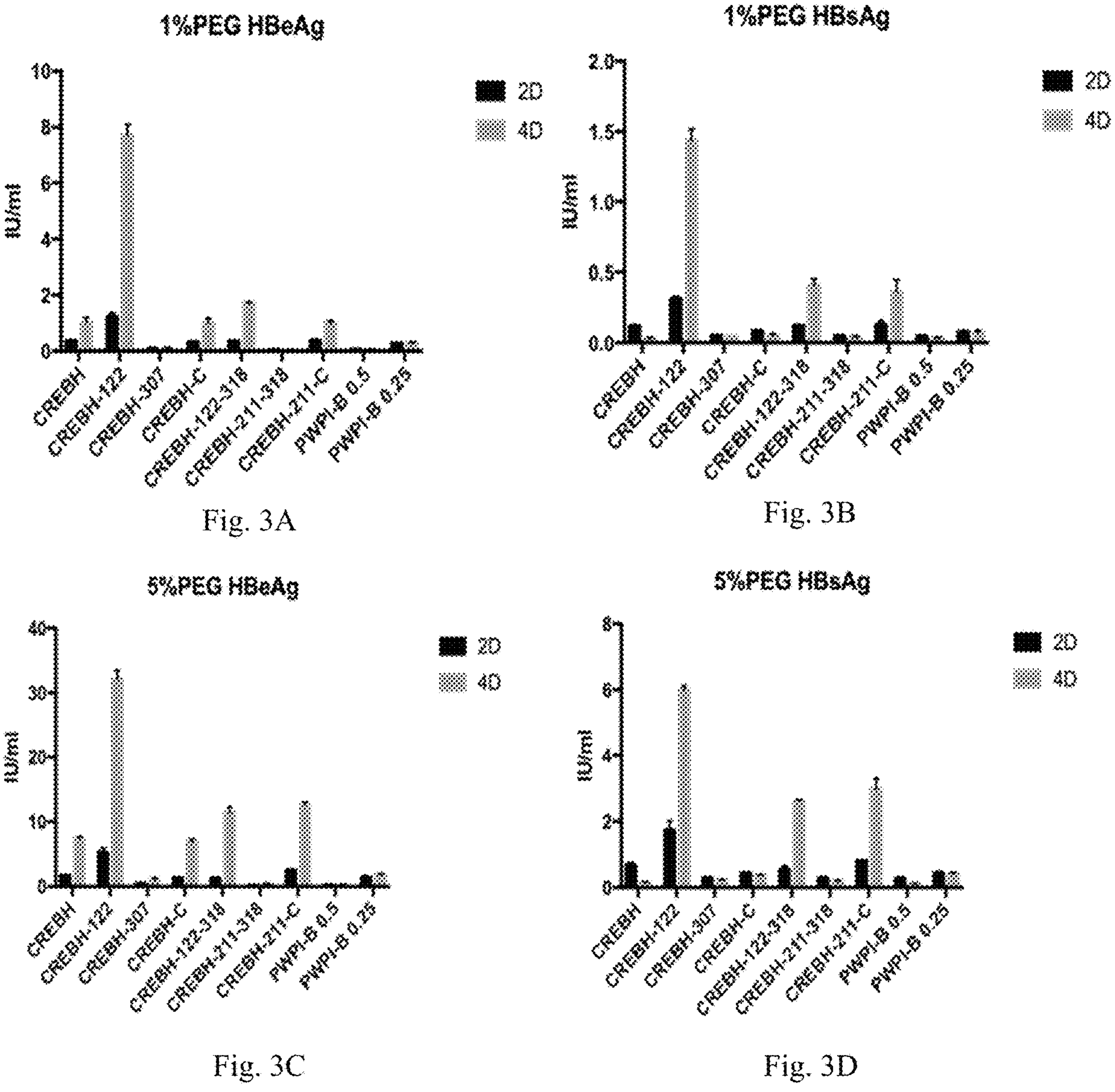
FIGS. 3A, 3B, 3C, and 3D show the effects of truncated forms of CREBH on HBV infection in Example 2.

Secondary structure of CREBH was predicted through experiments using the CFSSP (Chou and Fasman Secondary Structure Prediction server) database. In accordance with results of the prediction, 3 breakpoints were selected from the middle part of CREBH protein to construct altogether 6 truncated clones, as shown in FIG. 2.

Results of the secondary structure prediction show that within amino acids 1-122 there is a segment of secondary structure with a low score, which may be an intrinsic disorder region. Such a region in transcription factors is usually closely related to transcriptional activation activity. In order to maintain integrity of the bZIP domain as much as possible, the second breakpoint was selected at amino acid 211, and amino acid 318 near the transmembrane region was selected as the third breakpoint. A total of 6 truncated form clones of CREBH were constructed. For each of the clones, an HA tag was added to its N-terminus and a c-myc tag was added to its C-terminus.

4. Cellular Localization of Truncated Forms of CREBH

In order to study the localization of CREBH in HepG2 cell line, an HA tag was attached to the N-terminus of each of the CREBH and truncated forms thereof constructed above, and a c-myc tag was attached to the C-terminus thereof. HepG2-NTCP cells were transduced with lentivirus. The HA tag and the c-myc tag were stained to observe the localization of different truncated forms of CREBH in the cells.

Results of the staining show that in full-length clone of CREBH, the color on the N-terminus and the color on the C-terminus are slightly separated, with a small part of the N-terminus of CREBH being localized to the nucleus, while most of it remaining in the cytoplasm and overlapping with the color on the C-terminus. In the truncated clone CREBH-122, separation between the nuclear-localized N-terminus and the cytoplasmic-localized C-terminus is more apparent. This indicates that compared with the full-length CREBH, the N-terminus truncated CREBH-122 can be cleaved more efficiently, or the N-terminus domain of CREBH-122 is more stable in the nucleus. CREBH-C, CREBH-122-318, and CREBH-211-318 are localized in a similar pattern, i.e., being localized predominantly to the nucleus, while the shorter form CREBH-307 and CREBH-211-C lose their nuclear localization. This indicates that the nuclear localization signal of CREBH may be located within amino acids 211-318.

In order to detect whether each truncated form still had transcriptional activation ability, experiments were conducted by using the activation of APOA4 gene reported in the literature as an indicator of the transcriptional activation ability of CREBH. After the truncated forms were transduced into HepG2-NTCP cells, relative expression of APOA4 was detected. It was then found that the full-length CREBH had the strongest activation effect on APOA4 gene. CREBH-C also had relatively high activation efficiency, which however was about ⅓ of the activation efficiency of the full-length CREBH. Although the N-terminus of CREBH-C was the same as that of the full-length CREBH, the C-terminus of CREBH-C did not have the transmembrane region on the part that had been cleaved; it might be possible that it was this small region that affected the stability of the protein, thereby indirectly reducing the ability of CREBH-C to activate APOA4. CREBH-122 and CREBH-122-318 were also capable of activating APOA4 gene to some extent, but were much less capable than the full-length CREBH and CREBH-C, indicating that the part of the domain of CREBH capable of transcriptional activation was located within amino acids 1-122.

5. Roles of Truncated Forms of CREBH in HBV Infection

HepG2-NTCP cells were transduced with lentivirus embedded with CREBH and truncated forms thereof. After 24 hours, the cells were re-seeded in a culture plate, and the culture medium was changed to PMM. After 24 hours, the cells were infected with HBV in the presence of 1% PEG and 5% PEG respectively. Supernatant was collected every 2 days and assayed using an ELISA kit. Results of the infection are shown in FIGS. 3A-D. As can be seen from the results, compared with the PWPI-B empty control, the full-length CREBH, CREBH-122, CREBH-C, CREBH-122-318, and CREBH-211-C can all increase the infection efficiency in the presence of 1% PEG and 5% PEG. Among them, CREBH-122 exhibits an enhancement effect significantly higher than that of other experimental groups.

HBcAg staining was also performed in the experiments, and results were consistent with the ELISA results. In addition to the enhancement effects of CREBH as well as its truncated clones CREBH-122 and CREBH-122-318 on HBV infection, it was also observed that CREBH-307 and CREBH-211-318 to some certain extent inhibited the infection, which was consistent with the ELISA results. It was thus speculated that these two truncated forms might have exerted a dominant-negative effect.

In short, the enhancement effect of CREBH on HBV infection depends on its own transcriptional activation ability, and CREBH-122 can significantly increase HBV antigens and the number of stained HBcAg positive cells. For this reason, CREBH-122, instead of full-length CREBH, was used to study its specific mechanism of action in subsequent experiments.

6. Enhancement Effects of CREBH-122 on Infection at Different Viral Titers

In addition to being affected by PEG, in vitro HBV infection also relies on the titer of the virus used. Therefore, in experiments, CREBH-122 and CREBH-122-318 which had the strongest enhancement effects, as well as the truncated clone CREBH-211-318 which had a slightly inhibitory effect, were used to be in comparison to a PWPI empty control. Differences in infection efficiency at different viral titers were tested. If the infection occurred under completely ideal conditions, the index of the virus infection would be in a single-factor linear relationship with the amount of the virus used. If there were one or more other limiting factors, then the curve for the infection would fall out of linear correlation and the infection would decrease significantly with the decrease of the viral titer.

Specifically, HepG2-NTCP cells were transduced with lentivirus embedded with CREBH and truncated forms thereof. After 24 hours, the cells were reseeded in a culture plate, and cultured for 24 hours with the culture medium having been changed to PMM. With 160 ul virus/200 ul system under normal infection being calculated as a 100% viral titer, the virus was added to the infection system at a 50% titer, 25% titer, and 12.5% titer, and PMM was added to the volume. Infection with diluted HBV was performed in the presence of 1% PEG and 5% PEG, respectively. ELISA results of the infection show that CREBH and truncated forms thereof had the same effects on the infection at different viral tiers.

Figure 4A:
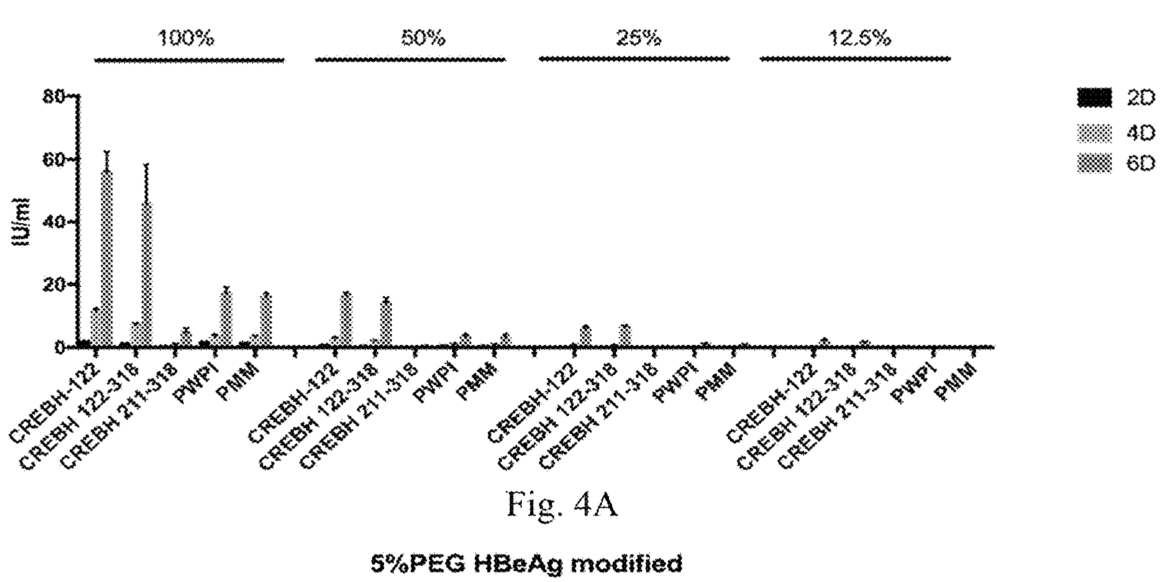
FIGS. 4A, 4B, and 4C show the results of infection at different viral titers after transduction of CREBH and truncated clones thereof in Example 2.
Figure 4B:
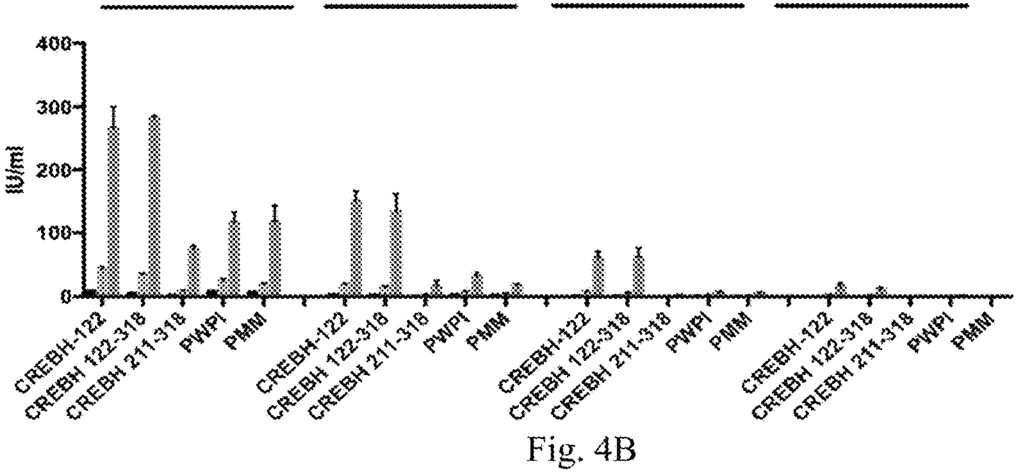

As can be seen from the results in FIG. 4A, in the presence of 1% PEG, the infection in the truncated form groups or the control group is reduced significantly with the decrease of the viral titer. As can be seen from the results in FIG. 4B, in the presence of 5% PEG, the reduction of the infection in cells transduced with CREBH-122 and CREBH-122-318 with the decrease of the viral titer is moderated.

Figure 4C:
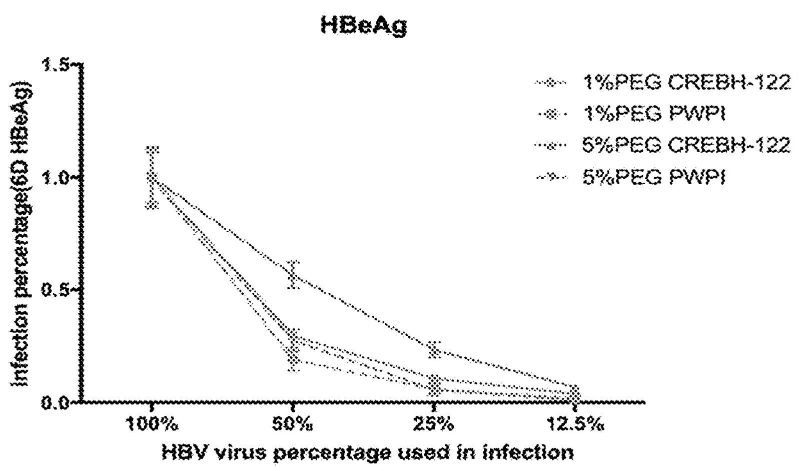
Figures 5A, 5B, 5C, 5D:
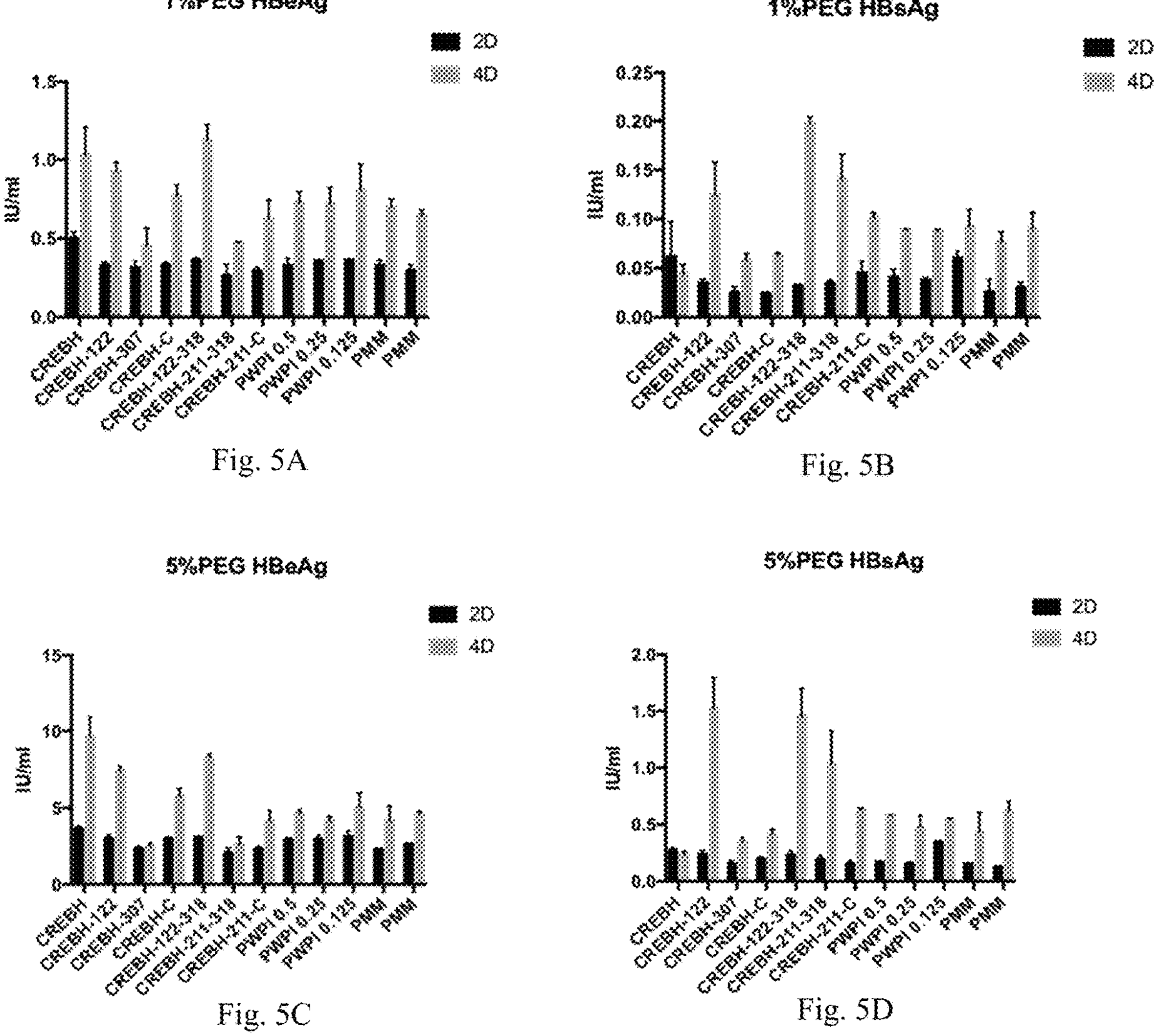
FIGS. 5A, 5B, 5C, and 5D are schematic diagrams showing effects of transduction of CREBH and truncated forms thereof after HBV infection in Example 2.

In order to demonstrate the results more clearly, HBeAg levels on Day 6 day after infection in the CREBH-122 group and the PWPI empty group were selected and used in the experiments for charting. For each group, HBeAg level at 100% virus infection was calculated as 100%, and infection values at other viral titers each were divided by this 100% to obtain percentages of the relative infection values (infection percentages). A line graph was drawn by taking the infection percentage as the ordinate and the viral titer as the abscissa, and results are shown in FIG. 4C. As can be seen from the figure, the curves obtained of the infection in the 1% PEG CREBH-122 group, the 1% PEG PWPI group, and the 5% PEG PWPI group are similar. Transduction of CREBH-122 in the presence of 5% PEG, however, remarkably renders the curve closer to be linear. Pearson r values were calculated and a higher correlation was seen in the 5% PEG CREBH-122 group (1% PEG CREBH-122=0.986, 1% PEG PWPI=0.968, 5% PEG=0.986, 5% PEG CREBH-122=0.994). This indicates that the transduction of CREBH-122 helped to overcome an important limiting factor for HBV infection of HepG2-NTCP.

7. Roles of CREBH after HBV Infection

Increases in secretion of HBeAg and HBsAg after HBV infection may be caused by enhanced transcription of HBV cccDNA or enhanced protein secretion pathway, and such increases cannot directly reflect enhancement in virus entry. Besides, CREBH itself has a transcriptional activation function. It is therefore necessary to detect in which specific step of the HBV infection CREBH exerts the enhancement effect.

As can be seen from the results shown in FIGS. 5A-D, first, in the experiments, CREBH and its truncated clones were transduced into the HepG2-NTCP cell line having been infected with HBV. Effects of CREBH and truncated forms thereof on HBeAg and HBsAg were consistent with those before the infection, indicating that CREBH might have indeed directly acted on HBV cccDNA itself. Second, HepG2-NTCP cells were transduced with lentivirus at 24 hours after the infection with HBV. Supernatant was collected every 2 days to measure HBeAg and HBsAg. Compared with their enhancement effects on the infection in the presence of 1% PEG, the enhancement effects of CREBH and truncated forms thereof were stronger on the infection in the presence of 5% PEG. This was likely because when the infection occurred in the presence of 5% PEG, more cccDNA were formed in the cells as templates for transcription. This indirectly demonstrates that the effect of CREBH is stronger, and further proves that CREBH can enhance the transcription of HBV.

Example 3: CREBH Affects HBV Infection without Altering NTCP

NTCP is a key receptor in HBV infection and can directly bind to the PreS1 region on the virus. Many factors capable of affecting HBV infection may indirectly affect HBV infection by affecting the expression level or cellular localization of NTCP. In order to detect whether CREBH enhances HBV infection by affecting NTCP, changes in NTCP mRNA level under the condition of overexpressing CREBH was first detected. Full-length CREBH as well as truncated forms CREBH-122 and CREBH-122-318 slightly down-regulated the NTCP mRNA level, and other truncated forms did not change the transcription of NTCP mRNA.

Example 4: CREBH Knockdown Inhibits HBV Infection

Figure 6A:
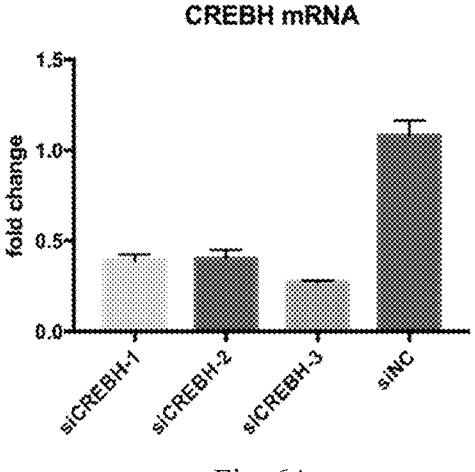
FIGS. 6A, 6B, and 6C are schematic diagrams showing the effects of knockdown of CREBH on infection in Example 4.
Figure 6B:
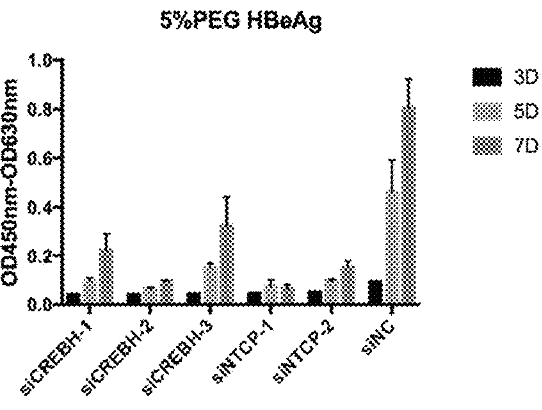
Figure 6C:
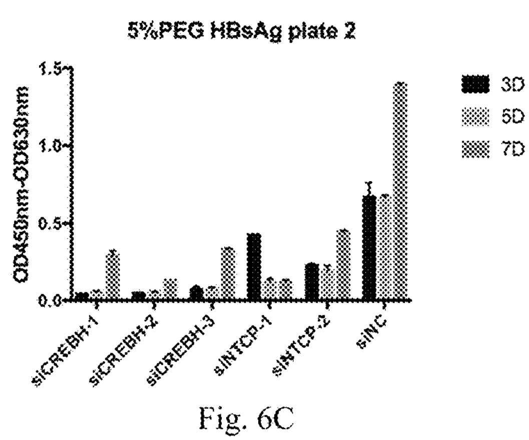
Figures 7A, 7B, 7C, 7D, 7E, 7F:
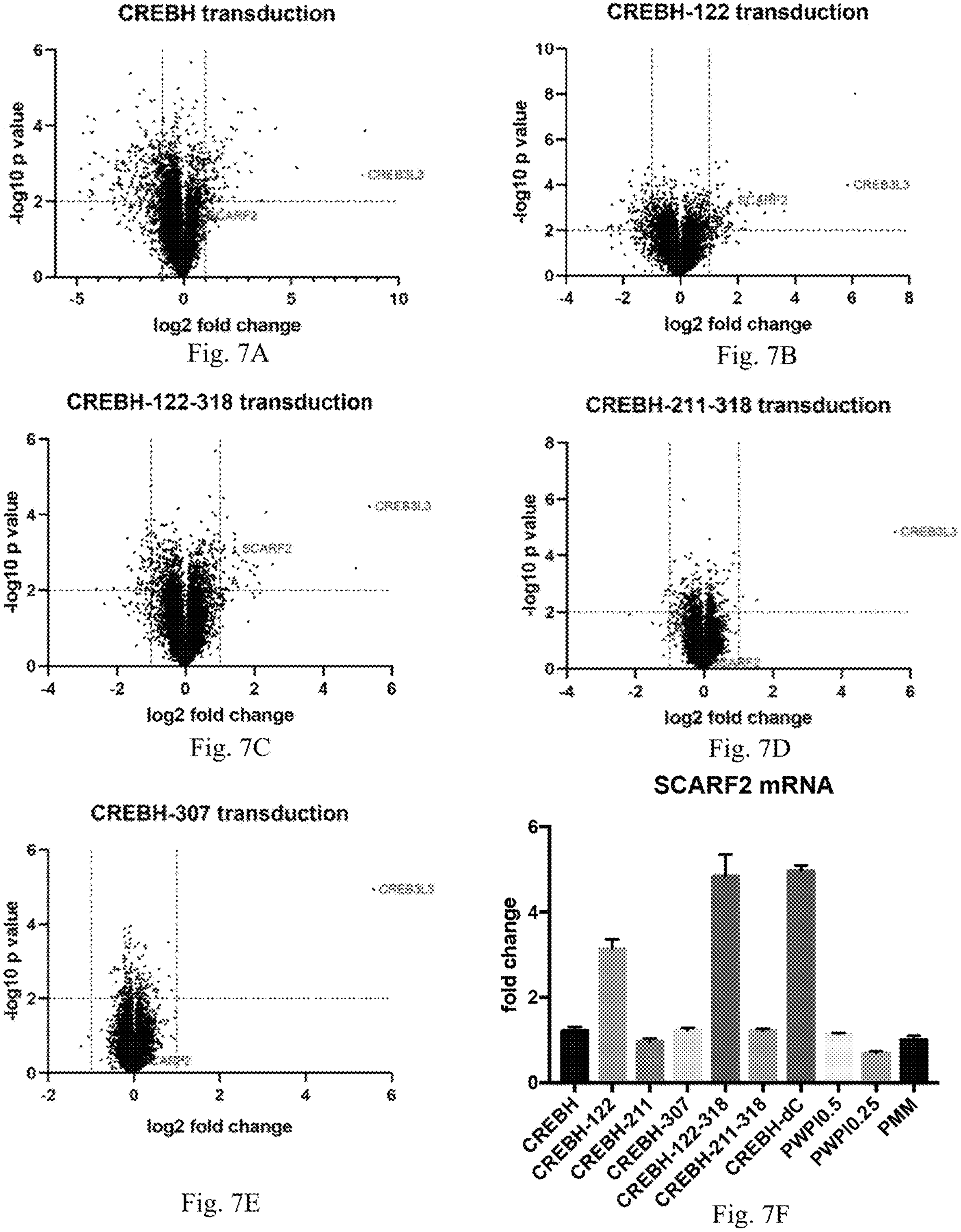
FIGS. 7A, 7B, 7C, 7D, 7E, and 7F are schematic diagrams showing the results of changes in expression of SCARF2 after transduction of CREBH and truncated forms thereof in Example 5.

To test necessity of CREBH in HBV infection, three CREBH-specific siRNAs were synthesized for knockdown experiments. qPCR results are shown in FIG. 6A. All the three siRNAs can effectively reduce CREBH mRNA level. In corresponding HBV infection experiments, two NTCP-specific siRNAs were synthesized for positive controls. After the CREBH siRNAs and the NTCP-specific siRNAs were separately transfected into HepG2-NTCP cells, HBV infection was performed. HBeAg and HBsAg in culture supernatant were detected respectively (results are shown in FIG. 6B and FIG. 6C respectively). As can be seen from the results, knockdown of CREBH can significantly affect and inhibit HBV infection to a degree that is comparable to the effect of knockdown of NTCP on the infection, which indicate that CREBH is important in HBV infection.

Example 5: Identification and Cloning of a CREBH-Regulated Host Factor

1. Transcriptome Sequencing Analysis of Truncated Forms of CREBH

Since the results of the infection occurred after the transduction of truncated forms of CREBH indicate that the transcriptional activation function of CREBH is necessary for enhancement of the infection, and the shortest functional truncated form CREBH-122-318 is localized on the nucleus, it is inferred that it is by activating a downstream gene that CREBH enhances HBV entry. In order to more accurately determine the downstream major gene, HepG2-NTCP cells transduced with CREBH, CREBH-122, CREBH-307, CREBH-122-318, CREBH-211-318, PWPI-B, and PMM were selected and used for transcriptome sequencing experiments. Meanwhile, CREBH siRNA-2 was selected and used to knock down CREBH in HepG2-NTCP cells. siNC was used as a negative control. Changes in transcriptomes were detected. Because a primary one of the known functions of CREBH is transcriptional activation, not transcriptional repression, genes that were up-regulated after the transduction as compared to the control group as well as genes that were down-regulated after CREBH knockdown as compared to the control group were analyzed.

Analysis results show that transcriptomes of the cells transduced with the full-length CREBH and the functional truncated forms CREBH-122 and CREBH-122-318 are similar to each other, while transcriptome characteristics of the cells transduced with the dominant negative CREBH-307 and CREBH-211-318 are similar to those of the cells in which CREBH is knocked down. This result is similar to the role of truncated clones in the infection, and it further confirms the location of the downstream major gene. Then, 62 overlapping genes that were up-regulated by 2-fold in the CREBH/PWPI group and down-regulated by more than 1.2-fold in the CREBH knockdown experiment were cloned and analyzed, by way of which SCARF2 gene was finally identified. Functions of SCARF2 gene were verified in later experiments.

2. SCARF2 is Regulated by CREBH and Truncated Clones Thereof

In order to more clearly demonstrate changes in expression of SCARF2 in cells transduced with CREBH and truncated forms thereof, corresponding mRNA sequencing data were displayed and analyzed by volcano plots. As shown in FIGS. 7A-F, CREBH can up-regulate the expression of SCARF2 gene, but not to a very significant level ($p<0.01$). However, the truncated forms CREBH-122 and CREBH-122-318, which have stronger enhancement effects on HBV infection, however, significantly up-regulates SCARF2. In contrast, the transduction with the truncated forms CREBH-211-318 and CREBH-307, which are incapable of HBV infection enhancement, does not lead to a change in SCARF2 expression. The same conclusion was also made from subsequent experiments using quantitative PCR, and the expression levels of SCARF2 were completely consistent with the enhancement effects of CREBH and its various truncated forms on HBV infection observed in the previous text. This indicates that SCARF2 may be a major gene for enhancement of HBV infection by CREBH.

Example 6: Effects of SCARF2 on Infection

1. SCARF2 Significantly Enhances HBV Infection

Figures 8A, 8B, 8C:
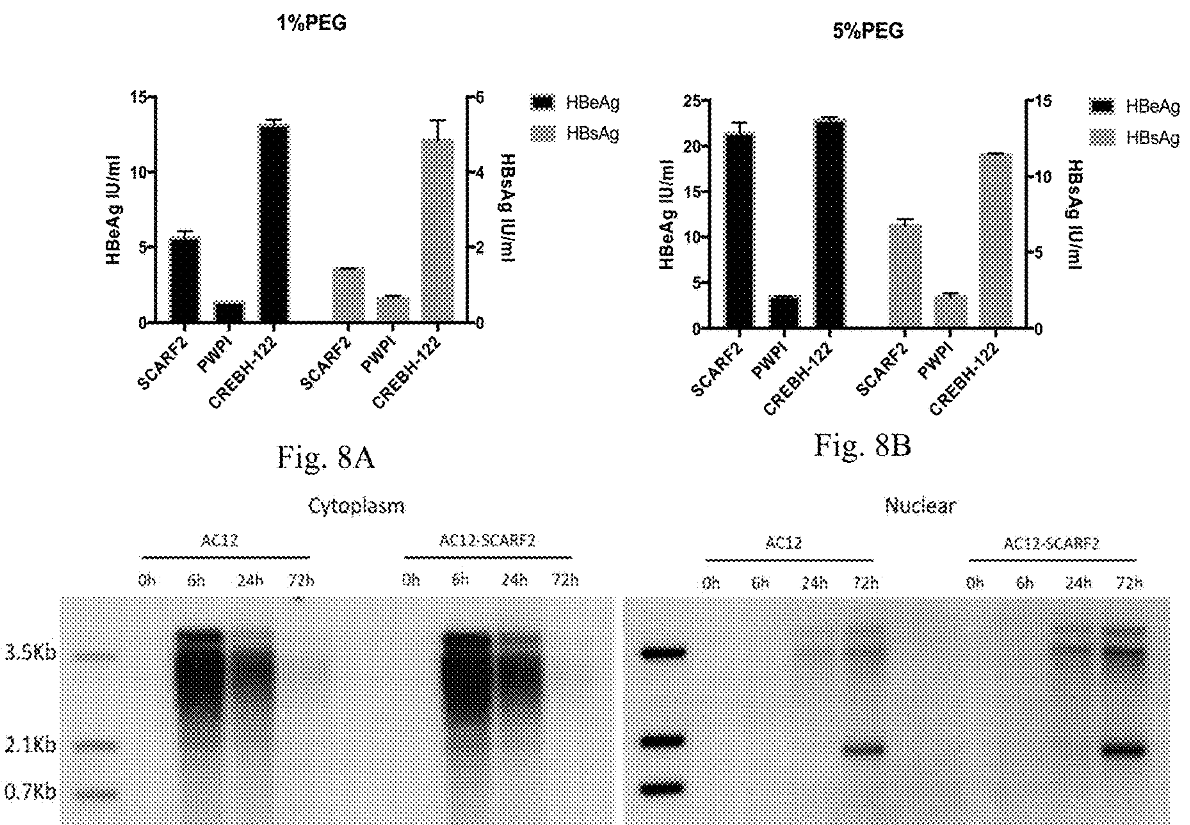
FIGS. 8A, 8B, and 8C are schematic diagrams showing the effects of transduction of SCARF2 on infection in Example 6.

In the present invention, SCARF2 was first overexpressed in HepG2-NTCP cell line to test the effects of SCARF2 on HBV infection. Results show that SCARF2 can enhance HBV infection in the presence of either 1% PEG or 5% PEG, with the enhancement effect being comparable to that of CREBH-122. Meanwhile, from HepG2-NTCP cell line stably expressing SCARF2, HBV DNA was isolated for analysis from the cytoplasm and the nucleus at different time points of HBV infection. Results are shown in FIGS. 8A-C and indicate that HBV DNA present in fractions of the cytoplasm of the cell expressing SCARF2 gene is slightly increased, while rcDNA and cccDNA present in fractions of the nucleus at a corresponding time point are detected to be significantly increased.

Figure 9A:
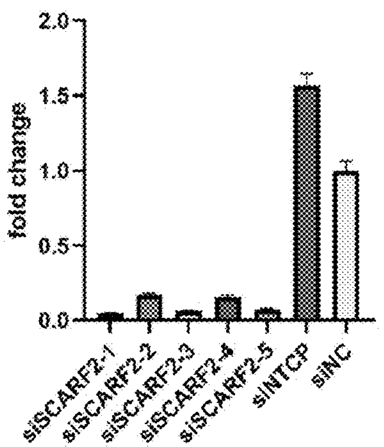
FIGS. 9A, 9B, and 9C are schematic diagrams showing the effects of knockdown of SCARF2 on infection in Example 6.
Figure 9B:
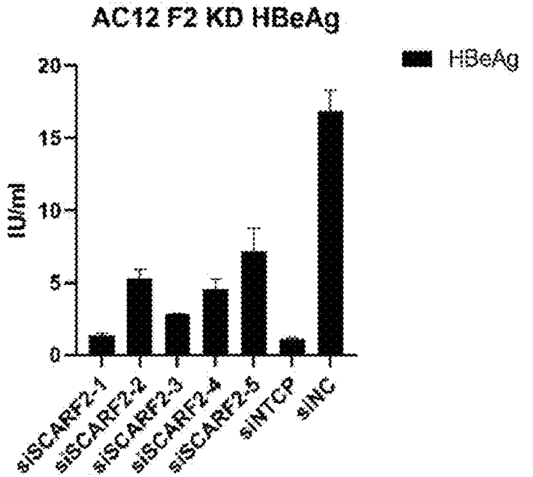
Figure 9C:
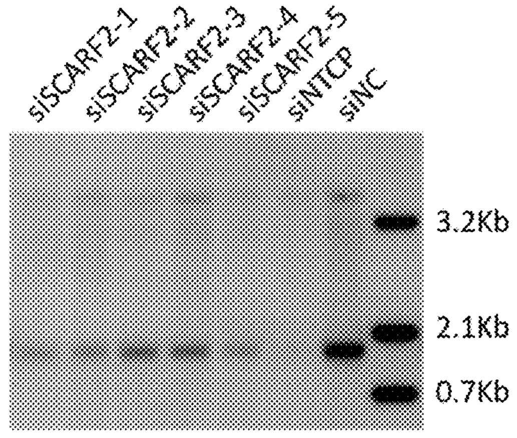

2. Knockdown of SCARF2 Inhibits HBV Infection 6 siRNAs were first synthesized to knock down SCARF2 in experiments. All the siRNAs could effectively reduce SCARF2 mRNA level. On this basis, HepG2-NTCP cells in which SCARF2 was knocked down were infected with HBV Results of the infection are shown in FIGS. 9A-C. HBV infection was effectively reduced in all the experimental groups with SCARF2 knockdown, with a degree of the reduction being similar to that of the reduction of the infection caused by NTCP knockdown. This indicates the importance of expression of SCARF2 gene in HBV infection.

3. Analysis of Structure and Functional Domains of SCARF2

Figure 10A:
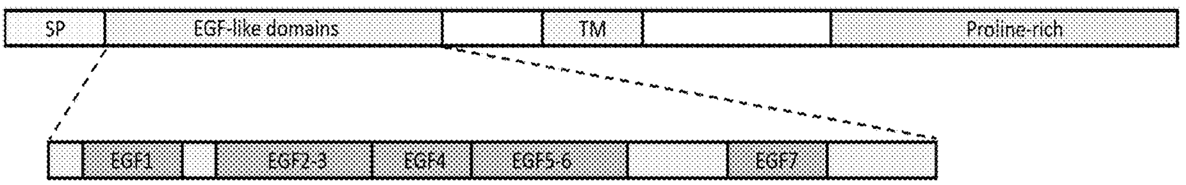
FIGS. 10A, 10B, and 10C are schematic diagrams showing the results of analysis of functions of domains of SCARF2 in Example 6.

SCARF2 gene is a type I transmembrane protein. SCARF2 gene can be structurally divided into four parts: signal peptides, an N-terminus domain containing 7 EGF-like domains, a transmembrane region, and a C-terminus domain containing a Proline-rich domain. As shown in FIG. 10A, from the topological structure of SCARF2, the N-terminus containing the EGF-like domains is located on the inner side of the lumen or the outer side of the cell membrane, and therefore the N-terminus domains are likely to be directly correlated to HBV during HBV infection. In order to find out whether the N-terminus EGF-like domains contained a crucial segment, mutant clones each with a different one of the 7 EGF-like domains deleted were constructed. EGF2 and EGF3, as well as EGF5 and EGF6 contained parts that overlapped each other, and therefore these parts that could not be completely separated were temporarily taken as a whole in constructing the deletion mutants.

Figure 10B:
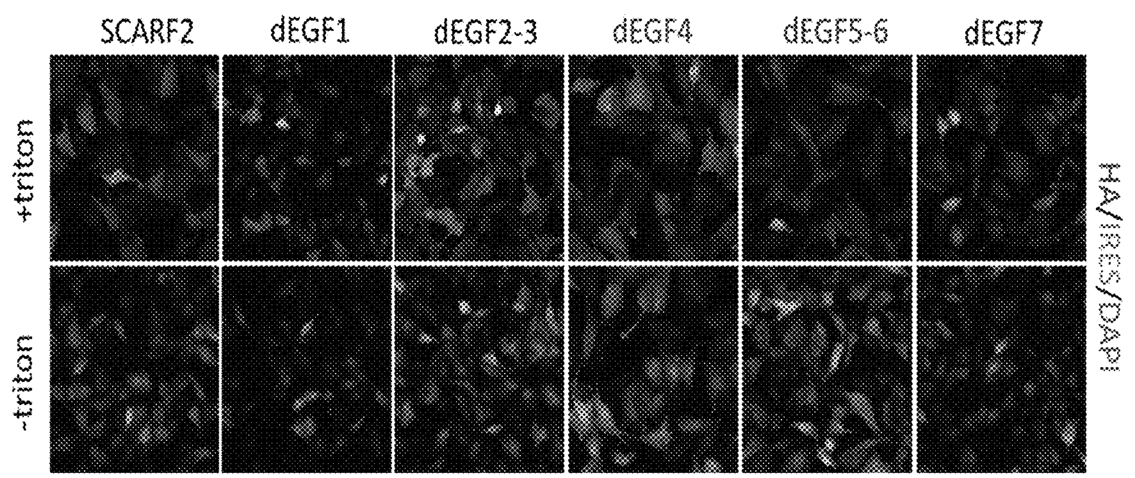
Figure 10C:
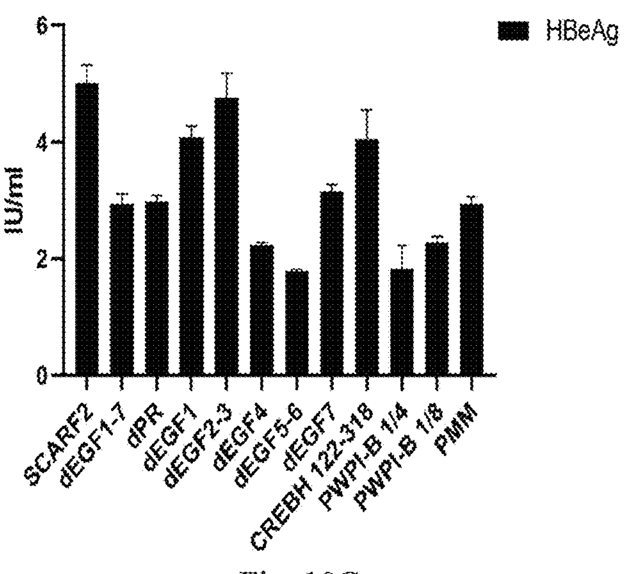
Figure 11A:
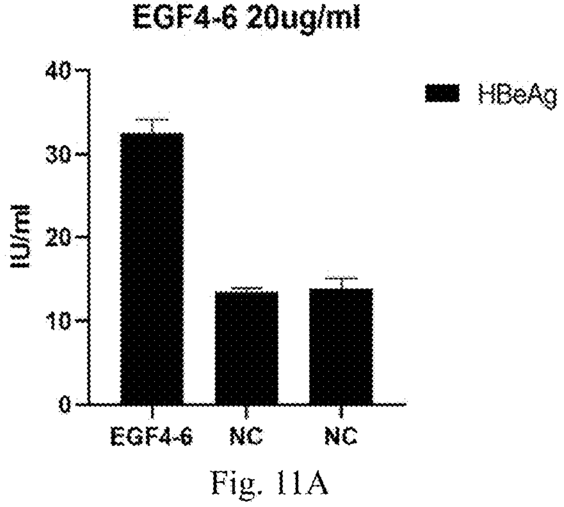
FIGS. 11A, 11B, 11C, and 11D are schematic diagrams showing the effects of exogenously expressed EGF4-6 protein on HBV infection tested in Example 7. EGF truncated protein was incubated at a concentration of 20 μg/mL with HBV, and then HBV infection was conducted. Judging from HBeAg level (FIG. 11A) and HBsAg level (FIG. 11B) in supernatant after the infection, addition of the protein could significantly enhance HBV infection.
Figure 11B:
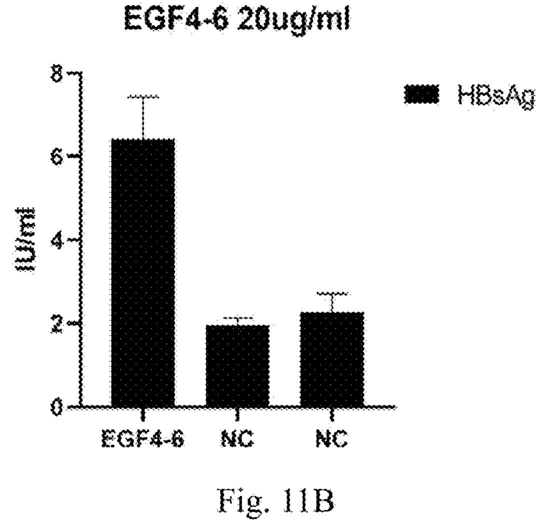
Figure 11C:
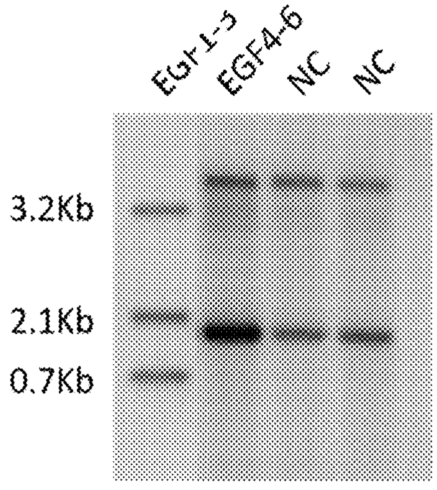
Figure 11C:
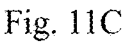
Figure 11D:
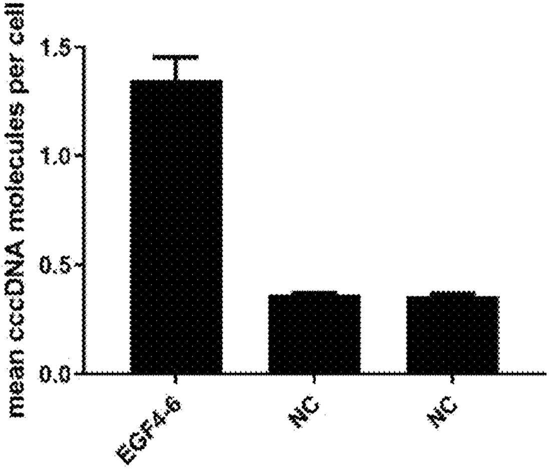

First, localization of each mutant of SCARF2 in a cell was determined by staining. Results are shown in FIG. 10B. Wild-type SCARF2 is localized to the cell membrane and cytoplasm; the EGF4 deletion mutant and the EGF5-6 deletion mutant are mainly localized to the cell membrane; and other mutants partially or completely lose their localization to the cell membrane. Consistent with results of HBV infection of corresponding mutants-overexpressed cell lines (FIG. 10C), overexpression of the two mutants with significantly increased cell membrane localization does not alter HBV infection efficiency, whereas the mutants with other EGFs deleted have enhancement effects on the infection that are comparable to the effect of wild-type SCARF2. It is thus proved that EGF4-6 of SCARF2 may be necessary for enhancing HBV infection, and that SCARF2 may function in the intracellular membrane system rather than on the cell membrane surface.

Example 7: Interaction of SCARF2 with HBV

1. Expression and Purification of Extracellular EGF Domains of SCARF2

In order to examine whether the N-terminus of SCARF2 could directly interact with HBV, in the present invention, the N-terminus of different N-terminus domain truncated forms of SCARF2 was labeled with an HA tag, and the C-terminus thereof was fused with a human Fc tag (IgG1), with a Precision tag being introduced between the two. The fusion protein was cloned into pCAGGs vector, and the plasmid was transfected into 293F cells and purified using Protein A Beads.

2. Effects of Truncated Proteins of SCARF2 on HBV Infection

In order to examine whether there was direct interaction between dSCARF2 proteins and HBV, in the experiment, proteins purified in vitro each were co-incubated at a concentration of 20 μg/mL with the virus, and HBV infection was conducted after the incubation. Early interaction between a virus and a soluble expressed nonfunctional receptor protein usually leads to loss and reduction of infectivity, and this method is also usually used to examine interaction between a protein and a virus. However, co-incubation of SCARF2 proteins with the virus could enhance the infection to some degree, and EGF4-6 could significantly enhance the infection (results are shown in FIGS. 11A-D). The results to some extent prove the interaction between the EGF-like domains of SCARF2 between the virus, and also indicate that the mode of action of SCARF2 is different from that of traditional viral receptors. It is known that soluble SCARF2 exists in blood, and soluble SCARF2 may have an enhancement effect on HBV infection.

3. Verification of Binding of SCARF2 Proteins to HBV by Equilibrium Density Gradient Centrifugation Binding of SCARF2 to the virus was also verified in the experiment by equilibrium density gradient centrifugation.

In equilibrium density gradient centrifugation, Nycodenz® was used as a medium, and different fractions of the virus were separated according to different densities thereof. In the experiment, the virus used was HBV produced by transfection of Huh7 cells. The virus produced as such contained a large amount of naked nucleocapsid fractions not enveloped by the viral envelope but having HBV DNA. These fractions, compared with completely enveloped virus particles, had a higher density, and therefore could be detected by qPCR detection for HBV DNA after being ultra-centrifugated so as to be separated from the later.

Figures 12A, 12B:
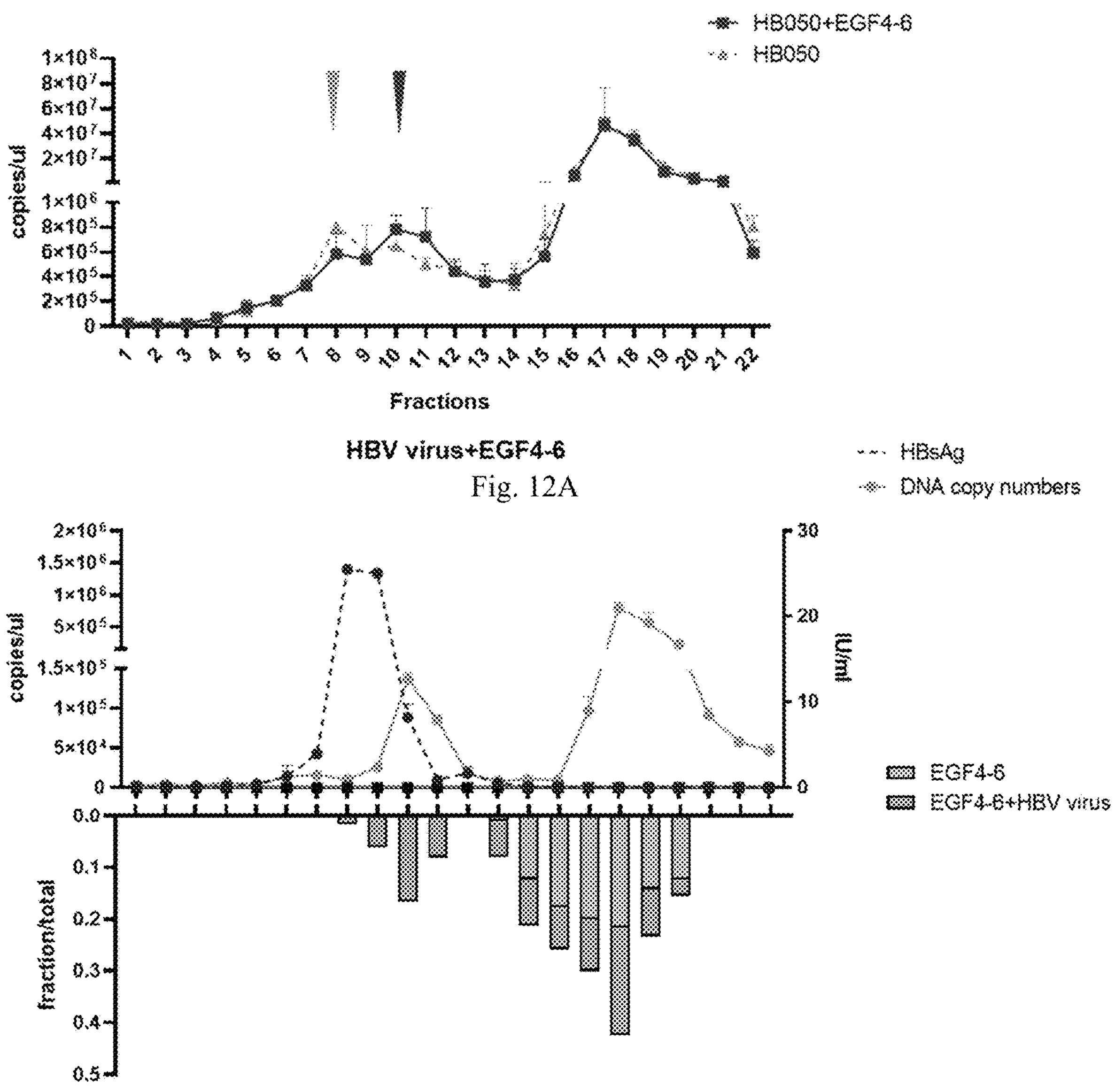
FIGS. 12A and 12B are schematic diagrams showing the direct interaction between EGF4-6 and HBV detected by equilibrium density gradient centrifugation in Example 7.

In the experiment, the virus was first incubated with SCARF2 EGF4-6 proteins and then centrifuged. Compared with the negative control without addition of the proteins, the addition of the two proteins caused the position of the virus particles to be shifted back by 2 fractions. This suggests that the binding of the proteins results in a change in the density of the viral particles and thus a change in the position of the viral particles in equilibrium density gradient centrifugation (results are shown in FIG. 12A).

Meanwhile, because the proteins added contained the HA tags, it was possible to detect SCARF2 EGF4-6 proteins contained in each of the fractions. After co-incubating of EGF4-6 with the virus, the fractions obtained by ultracentrifugation were subjected to a dot blot experiment (results are shown in FIG. 12B), and the content of EGF4-6 proteins in each of the fractions was measured by using an anti-HA antibody. Results were quantified by ImageJ and are shown in FIG. 12B (the lower chart). Compared with the control group without the virus, the co-incubating of EGF4-6 with the virus leads to detection of presence of the proteins in fractions 9-11, which position is consistent with the position (fractions 9-11) of intact particles of the virus but inconsistent with the position (fractions 7-10) of subviral particles (SVPs). This further verifies the interaction of the extracellular EGF domains of SCARF2 protein with HBV.

Figure 13A:
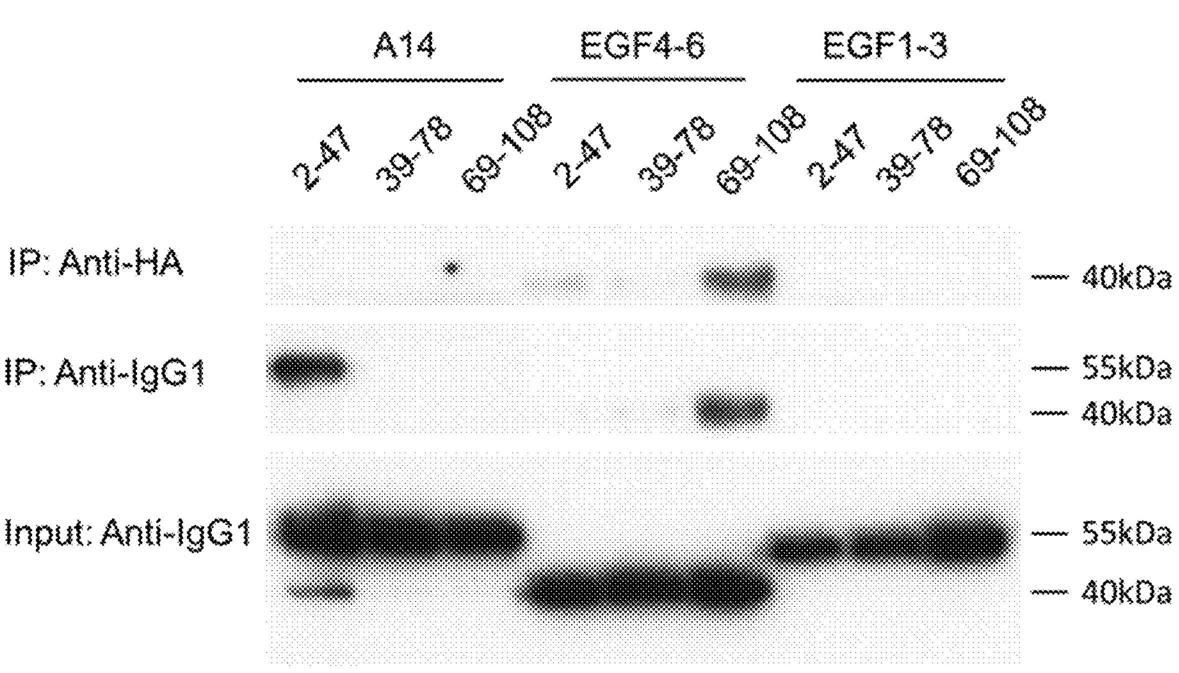
FIGS. 13A and 13B are schematic diagrams showing the results of interaction between EGF4-6 domains of SCARF2 and the amino acids 69-108 of the preS1 segment of HBV L protein in Example 7.
Figure 13B:
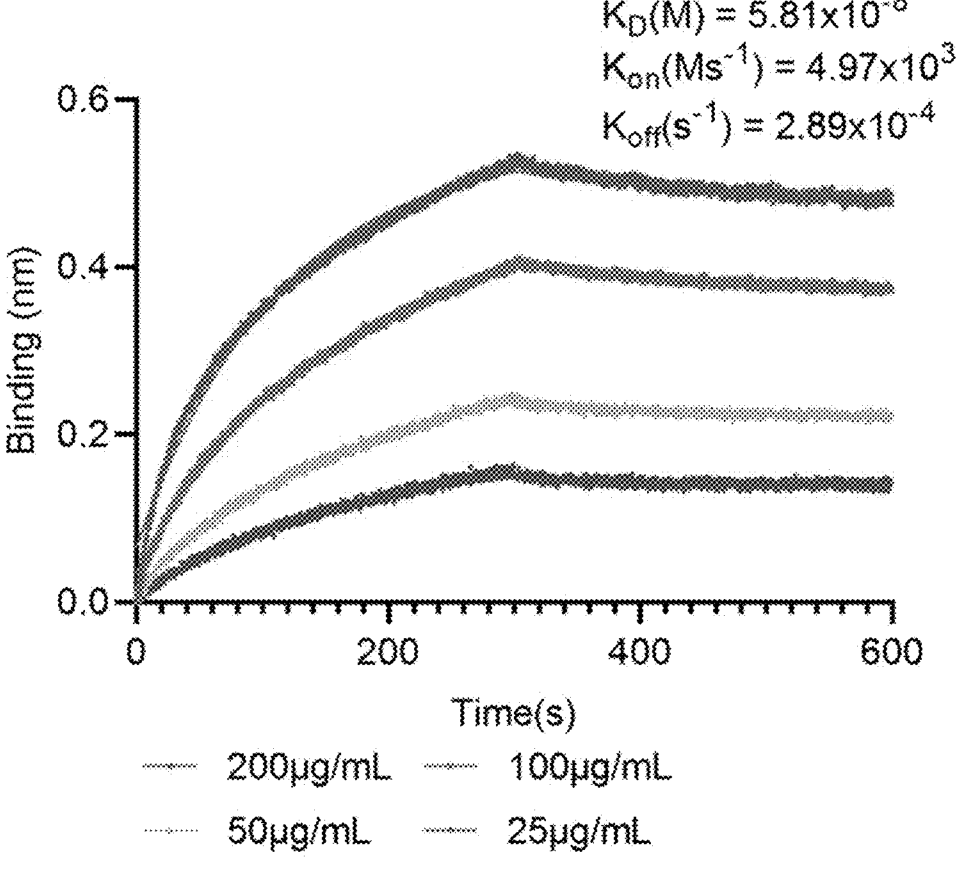

4. EGF4-6 Domains of SCARF2 Interact with Amino Acids 69-108 of the preS1 Segment of HBV L Protein Compared with SVPs, the virus particles were rich in L protein, and the main functional segment of L protein was the preS1 segment; it was therefore speculated that the SCARF2 EGF4-6 proteins interact with the preS1 segment of the L protein of the virus. In order to further prove protein binding sites, three partially overlapping polypeptides (peptide$^{2-48}$, peptide$^{39-78}$, and peptide$^{69-108}$) were first synthesized to cover the entire preS1 segment of the L protein of the virus. The C-terminus of each of the synthesized peptides was biotin labeled. It was found first by immunoprecipitation that the SCARF2 EGF4-6 proteins specifically bound to the polypeptide containing amino acids 69-108 of preS1 (peptide$^{69-108}$) (results are shown in FIG. 13A). Then, the binding force between the polypeptide and the SCARF2 EGF4-6 proteins was measured using the ForteBio Octet system, with dissociation constant ($K_d$) being determined to be 58 nM (results are shown in FIG. 13B). This experiment reveals specific, strong binding interaction between the SCARF2 protein and the virus.

Example 8: Mechanism of Action of SCARF2 in HBV Infection

1. HBV Infection Promotes Mutual Approach of SCARF2 and NTCP

Proximity ligation assay (PLA) is one of commonly used methods for detection of protein-protein interaction in living cells. Because HBV bound to its receptor NTCP during the infection, and experiments had proved the interaction between SCARF2 and HBV, it was therefore speculated that in the early stage of HBV infection, HBV entry would cause NTCP and SCARF2 to approach each other. The interaction between NTCP and SCARF2 at 48 hours of HBV infection was detected by PLA assay.

Figures 14A, 14B:
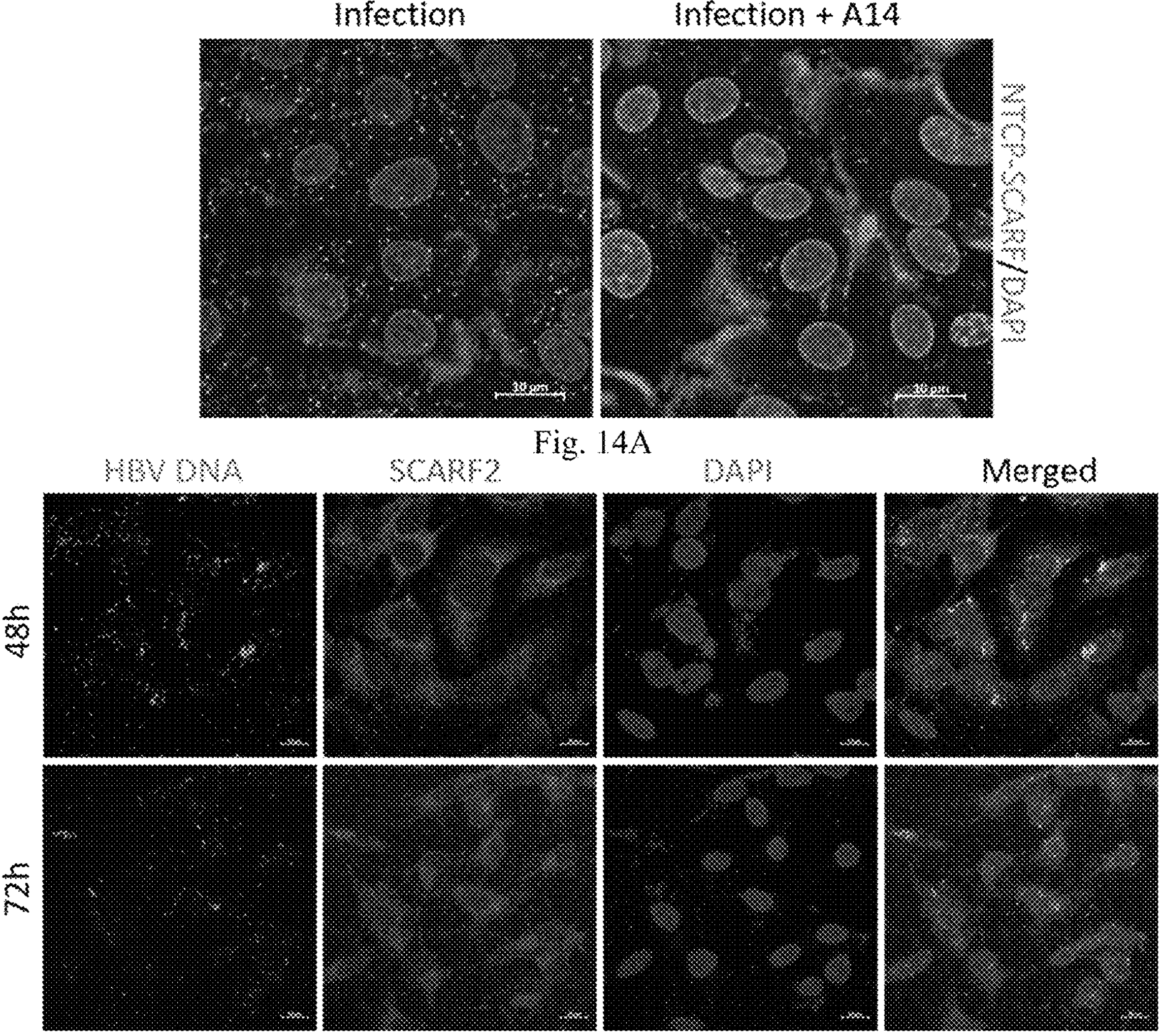
FIGS. 14A and 14B are schematic diagrams showing the results of intracellular localization of SCARF2, NTCP, and HBV DNA during HBV infection in Example 8.

FIGS. 14A-B are schematic diagrams showing the results of intracellular localization of SCARF2, NTCP, and HBV DNA during HBV infection. FIG. 14A shows the interaction between NTCP and SCARF2 during HBV infection labeled by proximity ligation assay (image on the left), and results of PLA after the infection was blocked using A14 antibody against the HBV preS1 region (image on the right). HBV infection significantly increased the interaction between NTCP and SCARF2. FIG. 14B shows subcellular localization of HBV DNA and SCARF2 protein in HepG2-NTCP cells at 48 hours (upper images) and 72 hours (lower images) after the cells were infected with HBV. HBV DNA in situ hybridization and SCARF2 protein immunofluorescence staining were performed. In experiments of the HBV infection, results of intracellular co-localization of the viral DNA and SCARF2 indicated that SCARF2 was involved in the process of HBV infection. Cell nuclei were stained with DAPI (A, B). As can be seen from the results, compared with the infection blocked group with addition of A14 antibody, the infection significantly increased the interaction between NTCP and SCARF2. In addition, co-localization of SCARF2 and the viral DNA was also found in the early stage of the infection by using HBV DNA in situ hybridization.

Figure 15A:
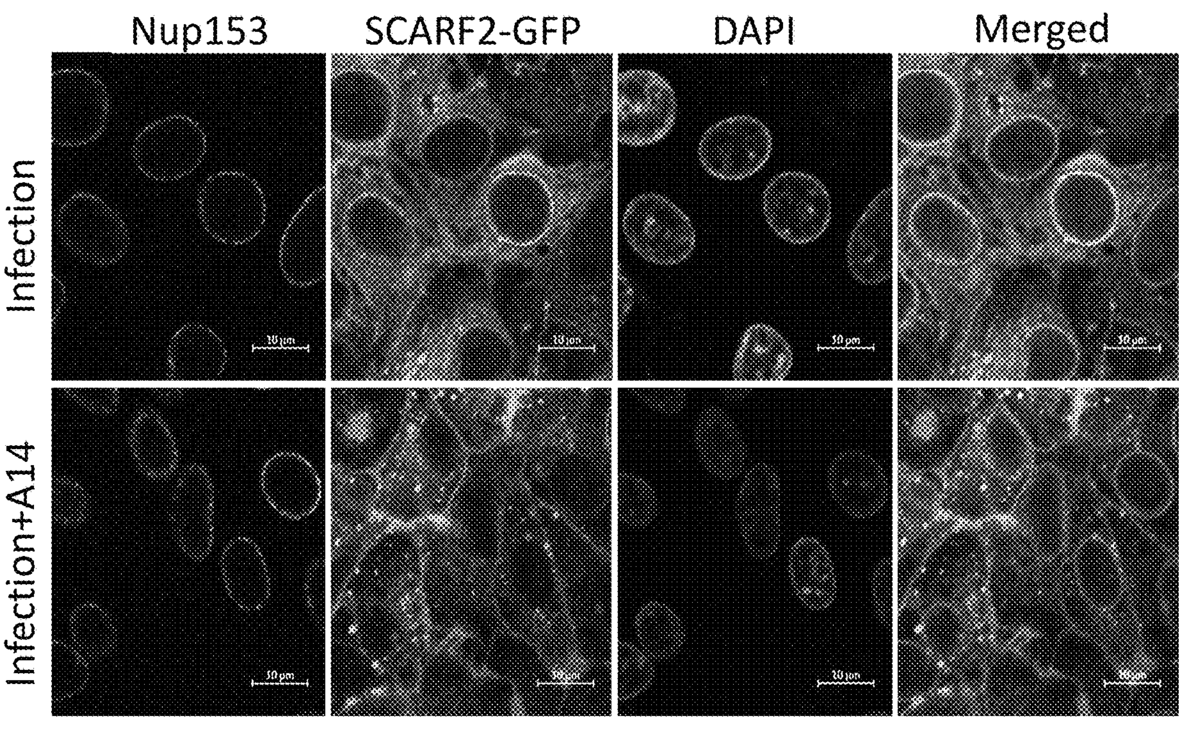
FIGS. 15A, 15B, 15C, and 15D are schematic diagrams showing the results of changes in localization of SCARF2 in the early stage of HBV infection in Example 7.
Figure 15B:
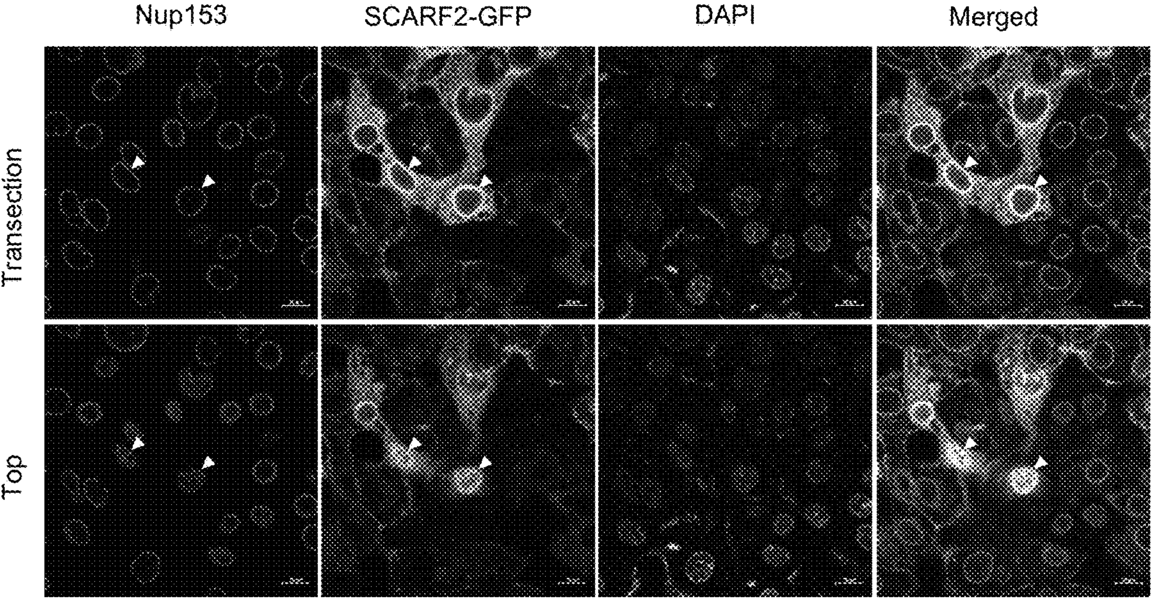
Figure 15C:
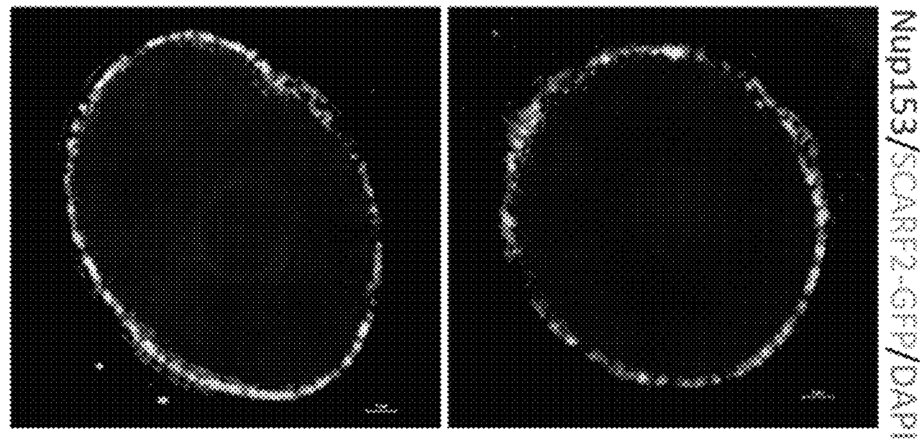
Figure 15D:
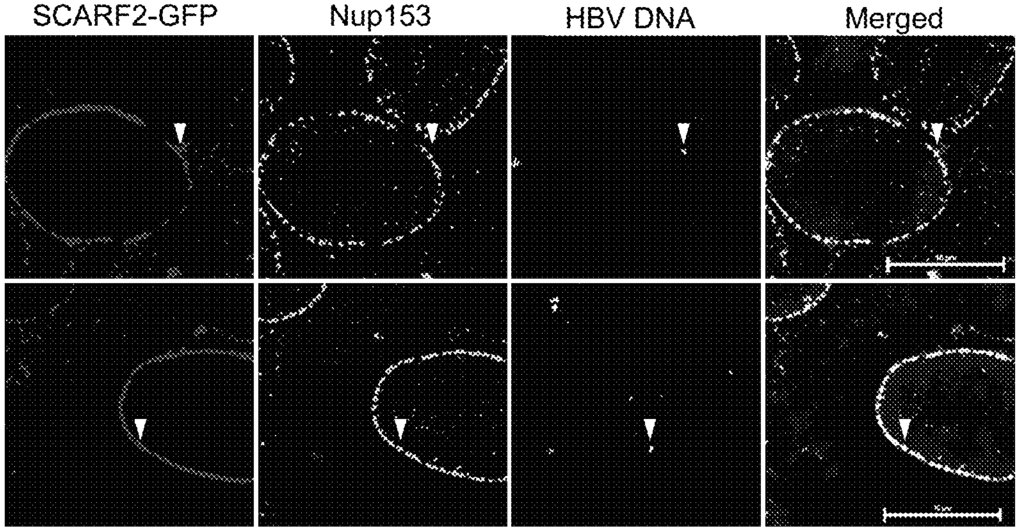

2. SCARF2 is Involved in Transportation of the Virus to the Nuclear Pore Complex To further understand the mechanism of action of SCARF2 in the process of HBV infection, a cell line stably expressing SCARF2-GFP protein was constructed using HepG2-NTCP cells. The localization of SCARF2 protein in the cells at 48 hours after HBV infection was observed by the fluorescence signal of GFP. As shown in FIG. 15A, compared with the infection blocked group with addition of the HBV A14 neutralizing antibody, the localization of SCARF2-GFP to the nuclear membrane was significantly increased at 48 hours after HBV infection. To further demonstrate the localization of SCARF2 to the nuclear membrane, HepG2-NTCP cells were transfected with SCARF2-GFP and cultured in PMM for 5 days to observe a positional relationship between SCARF2-GFP and the nuclear pore complex indicated by Nup153. As shown in FIG. 15B, co-localization of SCARF2-GFP and Nup153 to the nuclear membrane is observed from a section of the nucleus, and meanwhile the co-localization of SCARF2-GFP and the nuclear pore complex indicated by Nup153 can also be observed when focusing the microscope on the top of the nucleus. In the experiment, this structure was also reconstructed by using an N-SIM S super-resolution microscope. As can be seen from results shown in FIG. 15C, SCARF2-GFP is partially localized to a side of the cytoplasmic of the nuclear pore complex. At 48 hours after HBV infection, SCARF2-GFP, the nuclear pore complex, and HBV DNA signals were simultaneously observed using a super-resolution microscope, which clearly showed the co-localization of the three (results are shown in FIG. 15D). The above experimental results suggest that SCARF2 may have mediated the transport of the HBV particles to the nuclear pore complex during the entry of the virus particles.

Although the present invention has been described in detail above by way of general description, specific embodiments and tests, it is obvious to those skilled in the art that modifications or improvements can be made thereto on the basis of the present invention. Such modifications or improvements made without departing from the spirit of the present invention all fall within the protection scope of the present invention.

What is claimed is:

1. A cell expressing a truncated form of a first exogenous host factor specific for hepatitis B virus (HBV) infection, wherein the truncated form comprises an N-terminus domain of the first exogenous host factor, and wherein the truncated form of the first exogenous host factor consists of an amino acid sequence as shown in SEQ ID NO: 9 or 10.

2. The cell according to claim 1 further comprising a second exogenous host factor specific for HBV infection and/or a truncated form thereof capable of regulating expression or function of the first specific host factor, wherein the second exogenous host factor comprises an amino acid sequence as shown in SEQ ID NO:1, or has an amino acid sequence having at least 90% identity to the amino acid sequence as shown in SEQ ID NO:1.

3. The cell according to claim 2, wherein the truncated form of the second exogenous host factor comprises an amino acid sequence as shown in SEQ ID NO: 2, SEQ ID NO:3, or SEQ ID NO:4.

4. The cell according to claim 1, wherein the cell is selected from a group consisting of HepG2 cells, HepG2-NTCP cells, and primary human hepatocytes (PHHs).

5. The cell according to claim 1, wherein the cells are cultured in a medium containing DMSO and/or insulin.

6. The cell according to claim 5, wherein the medium is PMM medium.

* * * * *